United States Patent
Richter et al.

(12) 
(10) Patent No.: US 6,225,329 B1
(45) Date of Patent: May 1, 2001

(54) MODULATORS OF PROTEIN TYROSINE PHOSPHATASES (PTPASES)

(75) Inventors: Lutz Stefan Richter, Værløse; Henrik Sune Andersen, Lyngby; Josef Vagner, Værløse; Claus Bekker Jeppesen, Nivå; Niels Peter Hundahl Møller, Copenhagen; Sven Branner, Lyngby, all of (DK); Jing Su, New York, NY (US); Farid Bakir, San Diego; Luke Milburn Judge, La Jolla, both of CA (US)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 09/265,069

(22) Filed: Mar. 9, 1999

Related U.S. Application Data

(60) Provisional application No. 60/082,913, filed on Apr. 24, 1998, provisional application No. 60/082,914, filed on Apr. 24, 1998, and provisional application No. 60/093,638, filed on Jul. 21, 1998.

(30) Foreign Application Priority Data

| Mar. 12, 1998 | (DK) | .................................................. 0342/98 |
| Mar. 12, 1998 | (DK) | .................................................. 0345/98 |
| Apr. 3, 1998 | (DK) | .............................................. 1998 00472 |
| Apr. 3, 1998 | (DK) | .............................................. 1998 00479 |
| Jul. 15, 1998 | (DK) | .............................................. 1998 00940 |

(51) Int. Cl.$^7$ ............................... A61K 31/41; C07F 9/06; C07C 255/00; C07C 69/76; C07C 63/00

(52) U.S. Cl. .................. 514/359; 548/128; 548/131; 548/134; 548/146; 548/208; 548/215; 548/240; 548/250; 548/255; 548/262.2; 548/300.1; 548/127; 514/362; 514/363; 514/364; 514/365; 514/372; 514/374; 514/378; 514/381; 514/383; 514/396; 514/403; 514/617; 514/621; 514/625; 558/411; 560/8; 562/405

(58) Field of Search .................. 562/405; 558/411; 560/8; 514/617, 621, 625, 359, 362, 363, 364, 365, 372, 374, 378, 381, 383, 396, 403; 548/127, 128, 131, 134, 146, 208, 215, 240, 250, 255, 262.2, 300.1

(56) References Cited

U.S. PATENT DOCUMENTS

| 3,966,965 | * 6/1976 | Sellstedt et al. ..................... 424/309 |
| 3,987,192 | * 10/1976 | Wright .................................. 424/304 |
| 4,169,153 | 9/1979 | Wright ................................... 424/304 |
| 4,457,872 | 7/1984 | Murase et al. ......................... 560/22 |

FOREIGN PATENT DOCUMENTS

| 2413966 | 9/1974 | (DE) . |
| 0 030 436 | 6/1981 | (EP) . |
| 1 449 934 | 9/1976 | (GB) . |
| 1 493 338 | 11/1977 | (GB) . |

OTHER PUBLICATIONS

Bezuglyi, P.A. et al., Chemical Abstract, vol. 93, No. 10, p. 391 (Sep. 8, 1980).
Bezuglyi, P.A. et al., Chemical Abstract, vol. 93, No. 24, p. 318 (Dec. 15, 1980).

* cited by examiner

Primary Examiner—Mukund J. Shah
Assistant Examiner—Tamthom N. Truong
(74) Attorney, Agent, or Firm—Steve T. Zelson, Esq.; Carol E. Rozek, Esq.

(57) ABSTRACT

The present invention provides novel compounds of Formula 1, compositions containing these compounds, methods of their use, and methods of their manufacture, where such compounds are pharmacologically useful inhibitors of Protein Tyrosine Phosphatases (PTPase's) such as PTP1B, CD45, SHP-1, SHP-2, PTPα, LAR and HePTP or the like,

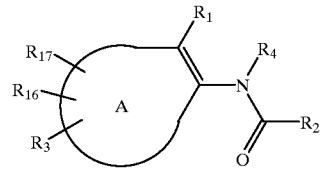

Formula 1 wherein A, $R_1$, $R_2$, $R_3$, $R_4$, $R_{16}$ and $R_{17}$ are as defined in the specification. The compounds are useful in the treatment of type I diabetes, type II diabetes, impaired glucose tolerance, insulin resistance, obesity, immune dysfunctions including autoimmunity diseases with dysfunctions of the coagulation system, allergic diseases including asthma, osteoporosis, proliferative disorders including cancer and psoriasis, diseases with decreased or increased synthesis or effects of growth hormone, diseases with decreased or increased synthesis of hormones or cytokines that regulate the release of/or response to growth hormone, diseases of the brain including Alzheimer's disease and schizophrenia, and infectious diseases.

13 Claims, No Drawings

MODULATORS OF PROTEIN TYROSINE PHOSPHATASES (PTPASES)

CROSS-REFERENCE TO RELATED APPLICATIONS

This application claims priority under 35 U.S.C. 119 of U.S. provisional applications 60/082,913 filed Apr. 24, 1998, 60/082,914 filed Apr. 24, 1998, 60/093,638 filed Jul. 21, 1998, and Danish applications 034/98 filed Mar. 12, 1998, 8/00345 filed Mar. 12, 1998, PA-1998-00472 filed Apr. 3, 1998, PA-1998-00479 filed Apr. 3, 1998 and PA 1998 00940 filed Jul. 15, 1998, the contents of which are fully incorporated herein by reference.

FIELD OF THE INVENTION

The present invention relates to novel compounds, to methods for their preparation, to compositions comprising the compounds, to the use of these compounds as medicaments and their use in therapy, where such compounds of Formula 1 are pharmacologically useful inhibitors of Protein Tyrosine Phosphatases (PTPases) such as PTP1B, CD45, SHP-1, SHP-2, PTPα, LAR and HePTP or the like,

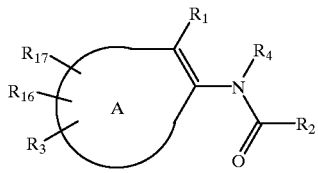

Formula 1 wherein A, $R_1$, $R_2$, $R_3$, $R_4$, $R_{16}$ and $R_{17}$ are defined more fully below. it has been found that PTPases play a major role in the intracellular modulation and regulation of fundamental cellular signalling mechanisms involved in metabolism, growth, proliferation and differentiation (Flint et al., The EMBO J. 12:1937–46 (1993); Fischer et al., Science 253:401–6 (1991)). Overexpression or altered activity of tyrosine phosphatases can also contribute to the symptoms and progression of various diseases (Wiener, et al., J. Natl. cancer Inst. 86:372–8 (1994); Hunter and Cooper, Ann. Rev. Biochem, 54:897–930 (1985)). Furthermore, there is increasing evidence which suggests that inhibition of these PTPases may help treat certain types of diseases such as diabetes type I and II, autoimmune disease, acute and chronic inflammation, osteoporosis and various forms of cancer.

BACKGROUND OF THE INVENTION

Protein phosphorylation is now well recognized as an important mechanism utilized by cells to transduce signals during different stages of cellular function (Fischer et al., Science 253:401–6 (1991); Flint et al., The EMBO J. 12:1937–46 (1993)). There are at least two major classes of phosphatases: (1) those that dephosphorylate proteins (or peptides) that contain a phosphate group(s) on a serine or threonine moiety (termed Ser/Thr phosphatases) and (2) those that remove a phosphate group(s) from the amino acid tyrosine (termed protein tyrosine phosphatases or PTPases).

The PTPases are a family of enzymes that can be classified into two groups: a) intracellular or nontransmembrane PTPases and b) receptor-type or transmembrane PTPases.

Intracellular PTPases: Most known intracellular type PTPases contain a single conserved catalytic phosphatase domain consisting of 220–240 amino acid residues. The regions outside the PTPase domains are believed to play important roles in localizing the intracellular PTPases subcellularly (Mauro, L. J. and Dixon, J. E. TIBS 19: 151–155 (1994)). The first intracellular PTPase to be purified and characterized was PTP1B which was isolated from human placenta (Tonks et al., J. Biol. Chem. 263: 6722–6730 (1988)). Shortly after, PTP1B was cloned (Charbonneau et al., Proc. Natl. Acad. Sci. USA 86: 5252–5256 (1989); Chemoff et al., Proc. Natl. Acad. Sci. USA 87: 2735–2789 (1989)). Other examples of intracellular PTPases include (1) T-cell PTPase (Cool et al. Proc. Natl. Acad. Sci. USA 86: 5257–5261 (1989)), (2) rat brain PTPase (Guan et al., Proc. Natl. Acad. Sci. USA 87:1501–1502 (1990)), (3) neuronal phosphatase STEP (Lombroso et al., Proc. Natl. Acad. Sci. USA 88: 7242–7246 (1991)), (4) ezrin-domain containing PTPases: PTPMEG1 (Guet al., Proc. Natl. Acad. Sci. USA 88: 5867–57871 (1991)), PTPH1 (Yang and Tonks, Proc. Natl. Acad. Sci. USA 88: 5949–5953 (1991)), PTPD1 and PTPD2 (Møller et al., Proc. Natl. Acad. Sci. USA 91: 7477–7481 (1994)), FAP-1/BAS (Sato et al., Science 268: 411–415 (1995); Banville et al., J. Biol. Chem. 269: 22320–22327 (1994); Maekawa et al., FEBS Letters 337: 200–206 (1994)), and SH2 domain containing PTPases: PTP1C/SH-PTP1/SHP-1 (Plutzky et al., Proc. Natl. Acad. Sci. USA 89:1123–1127 (1992); Shen et al., Nature Lond. 352: 736–739 (1991)) and PTP1D/Syp/SH-PTP2/SHP-2 (Vogel et al., Science 259: 1611–1614 (1993); Feng et al., Science 259: 1607–1611 (1993); Bastein et al., Biochem. Biophys. Res. Comm. 196: 124–133 (1993)).

Low molecular weight phosphotyrosine-protein phosphatase (LMW-PTPase) shows very little sequence identity to the intracellular PTPases described above. However, this enzyme belongs to the PTPase family due to the following characteristics: (i) it possesses the PTPase active site motif: Cys-Xxx-Xxx-Xxx-Xxx-Xxx-Arg (Cirri et al., Eur. J. Biochem. 214: 647–657 (1993)); (ii) this Cys residue forms a phospho-intermediate during the catalytic reaction similar to the situation with 'classical' PTPases (Cirri et al., supra; Chiarugi et al., FEBS Lett. 310: 9–12 (1992)); (iii) the overall folding of the molecule shows a surprising degree of similarity to that of PTP1B and Yersinia PTP (Su et al., Nature 370: 575–578 (1994)).

Receptor-type PTPases consist of a) a putative ligand-binding extracellular domain, b) a transmembrane segment, and c) an intracellular catalytic region. The structures and sizes of the putative ligand-binding extracellular domains of receptor-type PTPases are quite divergent. In contrast, the intracellular catalytic regions of receptor-type PTPases are very homologous to each other and to the intracellular PTPases. Most receptor-type PTPases have two tandemly duplicated catalytic PTPase domains.

The first receptor-type PTPases to be identified were (1) CD45/LCA (Ralph, S. J., EMBO J. 6:1251–1257 (1987)) and (2) LAR (Streuli et al., J. Exp. Med. 168: 1523–1530 (1988)) that were recognized to belong to this class of enzymes based on homology to PTP1B (Charbonneau et al., Proc. Natl. Acad. Sci. USA 86: 5252–5256 (1989)). CD45 is a family of high molecular weight glycoproteins and is one of the most abundant leukocyte cell surface glycoproteins and appears to be exclusively expressed upon cells of the hematopoietic system (Trowbridge and Thomas, Ann. Rev. Immunol. 12:85–116 (1994)).

The identification of CD45 and LAR as members of the PTPase family was quickly followed by identification and cloning of several different members of the receptor-type PTPase group. Thus, 5 different PTPases, (3) PTPα, (4)

PTPβ, (5) PTPδ, (6) PTPε, and (7) PTPζ, were identified in one early study (Krueger et al., *EMBO J.* 9: 3241–3252 (1990)). Other examples of receptor-type PTPases include (8) PTPγ (Bamea et al., *Mol. Cell. Biol.* 13:1497–1506 (1995)) which, like PTPζ (Krueger and Saito, *Proc. Natl. Acad. Sci USA* 89: 7417–7421 (1992)) contains a carbonic anhydrase-like domain in the extracellular region, (9) PTPμ (Gebbink et al., *FEBS Letters* 290: 123–130 (1991)), (10) PTPκ (Jiang et al., *Mol. Cell. Biol.* 13: 2942–2951 (1993)). Based on structural differences the receptor-type PTPases may be classified into subtypes (Fischer et al., *Science* 253: 401–406 (1991)): (I) CD45; (II) LAR, PTPd, (11) PTPσ; (III) PTPb, (12) SAP-1 (Matozaki et al.,*J. Biol. Chem.* 269: 2075–2081 (1994)), (13) PTP-U2/GLEPP1 (Seimiya et al., *Oncogene* 10: 1731–1738 (1995); Thomas et al., *J. Biol. Chem.* 269:19953–19962 (1994)), and (14) DEP-1; (IV) PTPa,_PTPe. All receptor-type PTPases except Type IV contain two PTPase domains. Novel PTPases are continuously identified, and it is anticipated that more than 500 different species will be found in the human genome, i.e., close to the predicted size of the protein tyrosine kinase superfamily (Hanks and Hunter, *FASEB J.* 9: 576–596 (1995)).

PTPases are the biological counterparts to protein tyrosine kinases (PTKs). Therefore, one important function of PTPases is to control, down-regulate, the activity of PTKs. However, a more complex picture of the function of PTPases now emerges. Several studies have shown that some PTPases may actually act as positive mediators of cellular signalling. As an example, the SH2 domain-containing PTP1D seems to act as a positive mediator in insulin-stimulated Ras activation (Noguchi et al., *Mol. Cell. Biol.* 14: 6674–6682 (1994)) and of growth factor-induced mitogenic signal transduction (Xiao et al., *J. Biol. Chem.* 269: 21244–21248 (1994)), whereas the homologous PTP1C seems to act as a negative regulator of growth factor-stimulated proliferation (Bignon and Siminovitch, *Clin.Immunol. Immunopathol.* 73: 168–179 (1994)). Another example of PTPases as positive regulators has been provided by studies designed to define the activation of the Src-family of tyrosine kinases. In particular, several lines of evidence indicate that CD45 is positively regulating the activation of hematopoietic cells, possibly through dephosphorylation of the C-terminal tyrosine of Fyn and Lck (Chan et al., *Annu. Rev. Immunol.* 12: 555–592 (1994)).

Dual specificity protein tyrosine phosphatases (dsPTPases) define a subclass within the PTPases family that can hydrolyze phosphate from phosphortyrosine as well as from phosphor-serine/threonine. dsPTPases contain the signature sequence of PTPases: His-Cys-Xxx-Xxx-Gly-Xxx-Xxx-Arg. At least three dsPTPases have been shown to dephosphorylate and inactivate extracellular signal-regulated kinase (ERKs)/mitogen-activated protein kinase (MAPK): MAPK phosphatase (CL100, 3CH134) (Charles et al., *Proc. Natl. Acad. Sci. USA* 90: 5292–5296 (1993)); PAC-1 (Ward et al., *Nature* 367: 651–654 (1994)); rVH6 (Mourey et al., *J. Biol. Chem.* 271: 3795–3802 (1996)). Transcription of dsPTPases are induced by different stimuli, e.g., oxidative stress or heat shock (Ishibashi et al.,*J. Biol. Chem.* 269: 29897–29902 (1994); Keyse and Emslie, *Nature* 359: 644–647 (1992)). Further, they may be involved in regulation of the cell cycle: cdc25 (Millar and Russell, *Cell.* 68: 407–410 (1992)); KAP (Hannon et al., *Proc. Natl. Acad. Sci USA* 91:1731–1735 (1994)). Interestingly, tyrosine dephosphorylation of cdc2 by a dual specific phosphatase, cdc25, is required for induction of mitosis in yeast (review by Walton and Dixon, *Annu. Rev. Biochem.* 62: 101–120 (1993)).

PTPases were originally identified and purified from cell and tissue lysates using a variety of artificial substrates and therefore their natural function of dephosphoryiation was not well known. Since tyrosine phosphorylation by tyrosine kinases is usually associated with cell proliferation, cell transformation and cell differentiation, it was assumed that PTPases were also associated with these events. This association has now been proven to be the case with many PTPases. PTP1B, a phosphatase whose structure was recently elucidated (Barford et al., Science 263:1397–1404 (1994)) has been shown to be involved in insulin-induced oocyte maturation (Flint et al., The EMBO J. 12:1937–46 (1993)) and recently it has been suggested that the overexpression of this enzyme may be involved in $p185^{c\text{-}erb\ B2}$-associated breast and ovarian cancers (Wiener, et al., J. Natl. cancer Inst. 86:372–8 (1994); Weiner et al., Am. J. Obstet. Gynecol. 170:1177–883 (1994)). The insulin-induced oocyte maturation mechanism has been correlated with the ability of PTP1B to block activation of S6 kinase. The association with cancer is recent evidence which suggests that overexpression of PTP1B is statistically correlated with increased levels of $p185^{c\text{-}erb\ B2}$ in ovarian and breast cancer. The role of PTP1B in the etiology and progression of the disease has not yet been elucidated. Inhibitors of PTP1B may therefore help clarify the role of PTP1B in cancer and in some cases provide therapeutic treatment for certain forms of cancer.

The activity of a number of other newly discussed phosphatases are currently under investigation. Two of these: SHP-1 and Syp/PTP1D/SHPTP2/PTP2C/SHP-2 have recently been implicated in the activation of Platelet Derived Growth Factor and Epidermal Growth Factor induced responses (Li et al., Mole. Cell. Biol. 14:509–17 (1994)). Since both growth factors are involved in normal cell processing as well as disease states such as cancer and arteriosclerosis, it is hypothesized that inhibitors of these phosphatases would also show therapeutic efficacy. Accordingly, the compounds of the present invention which exhibit inhibitory activity against various PTPases, are indicated in the treatment or management of the foregoing diseases.

PTPases: the insulin receptor signalling pathway/diabetes

Insulin is an important regulator of different metabolic processes and plays a key role in the control of blood glucose. Defects related to its synthesis or signalling lead to diabetes mellitus. Binding of insulin to its receptor causes rapid (auto)phosphorylation of several tyrosine residues in the intracellular part of the b-subunit. Three closely positioned tyrosine residues (the tyrosine-1150 domain) must all be phosphorylated to obtain full activity of the insulin receptor tyrosine kinase (IRTK) which transmits the signal further downstream by tyrosine phosphorylation of other cellular substrates, including insulin receptor substrate-1 (IRS-1) (Wilden et al., J. Biol. Chem. 267: 16660–16668 (1992); Myers and White, *Diabetes* 42: 643–650 (1993); Lee and Pilch,*Am. J. Physiol.* 266: C319–C334 (1994); White et al., J. Biol. Chem. 263: 2969–2980 (1988)). The structural basis for the function of the tyrosine-triplet has been provided by recent X-ray crystallographic studies of IRTK that showed tyrosine-1150 to be autoinhibitory in its unphosphorylated state (Hubbard et al., *Nature* 372: 746–754 (1994)).

Several studies clearly indicate that the activity of the auto-phosphorylated IRTK can be reversed by dephosphorylation in vitro (reviewed in Goldstein, *Receptor* 3: 1–15 (1993); Mooney and Anderson, *J. Biol. Chem.* 264: 6850–6857 (1989)), with the tri-phosphorylated tyrosine-1150 domain being the most sensitive target for protein-tyrosine phosphatases (PTPases) as compared to the di- and mono-phosphorylated forms (King et al., *Biochem. J.* 275: 413–418 (1991)). It is, therefore, tempting to speculate that this tyrosine-triplet functions as a control switch of IRTK activity. Indeed, the IRTK appears to be tightly regulated by PTP-mediated dephosphorylation in vivo (Khan et al., *J. Biol. Chem.* 264: 12931–12940 (1989); Faure et al., *J. Biol. Chem.* 267: 11215–11221 (1992); Rothenberg et al., *J. Biol. Chem.* 266: 8302–8311 (1991)). The intimate coupling of PTPases to the insulin signalling pathway is further evidenced by the finding that insulin differentially regulates PTPase activity in rat hepatoma cells (Meyerovitch et al., *Biochemistry* 31: 10338–10344 (1992)) and in livers from alloxan diabetic rats (Boylan et al., *J. Clin. Invest.* 90: 174–179 (1992)).

Relatively little is known about the identity of the PTPases involved in IRTK regulation. However, the existence of PTPases with activity towards the insulin receptor can be demonstrated as indicated above. Further, when the strong PTPase-inhibitor pervanadate is added to whole cells an almost full insulin response can be obtained in adipocytes (Fantus et al., *Biochemistry* 28: 8864–8871 (1989); Eriksson et al., *Diabetologia* 39: 235–242 (1995)) and skeletal muscle (Leighton et al., *Biochem. J.* 276: 289–292 (1991)). In addition, recent studies show that a new class of peroxovanadium compounds act as potent hypoglycemic compounds in vivo (Posner et al., supra). Two of these compounds were demonstrated to be more potent inhibitors of dephosphorylation of the insulin receptor than of the EGF-receptor.

It was recently found that the ubiquitously expressed SH2 domain containing PTPase, PTP1D (Vogel et al., 1993, supra), associates with and dephosphorylates IRS-1, but apparently not the IR itself (Kuhné et al., *J. Biol. Chem.* 268: 11479–11481 (1993); (Kuhné et al., *J. Biol. Chem.* 269:15833–15837 (1994)).

Previous studies suggest that the PTPases responsible for IRTK regulation belong to the class of membrane-associated (Faure et al., *J. Biol. Chem.* 267: 11215–11221 (1992)) and glycosylated molecules (Häring et al., *Biochemistry* 23: 3298–3306 (1984); Sale, *Adv. Prot. Phosphatases* 6: 159–186 (1991)). Hashimoto et al. have proposed that LAR might play a role in the physiological regulation of insulin receptors in intact cells (Hashimoto et al., *J. Biol. Chem.* 267: 13811–13814 (1992)). Their conclusion was reached by comparing the rate of dephosphorylation/inactivation of purified IR using recombinant PTP1B as well as the cytoplasmic domains of LAR and PTPa. Antisense inhibition was recently used to study the effect of LAR on insulin signalling in a rat hepatoma cell line (Kulas et al., *J. Biol. Chem.* 270: 2435–2438 (1995)). A suppression of LAR protein levels by about 60 percent was paralleled by an approximately 150 percent increase in insulin-induced autophosphorylation. However, only a modest 35 percent increase in IRTK activity was observed, whereas the insulin-dependent phosphatidylinositol 3-kinase (PI 3-kinase) activity was significantly increased by 350 percent. Reduced LAR levels did not alter the basal level of IRTK tyrosine phosphorylation or activity. The authors speculate that LAR could specifically dephosphorylate tyrosine residues that are critical for PI 3-kinase activation either on the insulin receptor itself or on a downstream substrate.

While previous reports indicate a role of PTPa in signal transduction through src activation (Zheng et al., *Nature* 359: 336–339 (1992); den Hertog et al., *EMBO J.* 12: 3789–3798 (1993)) and interaction with GRB2 (den Hertog et al., *EMBO J.* 13: 3020–3032 (1994); Su et al., *J. Biol. Chem.* 269: 18731–18734 (1994)), a recent study suggests a function for this phosphatase and its close relative PTPe as negative regulators of the insulin receptor signal (Møller et al., 1995 supra). This study also indicates that receptor-like PTPases play a significant role in regulating the IRTK, whereas intracellular PTPases seem to have little, if any, activity towards the insulin receptor. While it appears that the target of the negative regulatory activity of PTPases a and e is the receptor itself, the downmodulating effect of the intracellular TC-PTP seems to be due to a downstream function in the IR-activated signal. Although PTP1B and TC-PTP are closely related, PTP1B had only little influence on the phosphorylation pattern of insulin-treated cells. Both PTPases have distinct structural features that determine their subcellular localization and thereby their access to defined cellular substrates (Frangione et al., *Cell.* 68: 545–560 (1992); Faure and Posner, *Glia* 9: 311–314 (1993)). Therefore, the lack of activity of PTP1B and TC-PTP towards the IRTK may, at least in part, be explained by the fact that they do not co-localize with the activated insulin receptor. In support of this view, PTP1B and TC-PTP have been excluded as candidates for the IR-associated PTPases in hepatocytes based on subcellular localization studies (Faure et al., *J. Biol. Chem.* 267: 11215–11221 (1992)).

The transmembrane PTPase CD45, which is believed to be hematopoietic cell-specific, was in a recent study found to negatively regulate the insulin receptor tyrosine kinase in the human multiple myeloma cell line U266 (Kulas et al., *J. Biol. Chem.* 271: 755–760 (1996)).

PTPases: somatostatin

Somatostatin inhibits several biological functions including cellular proliferation (Lamberts et al., *Molec. Endocrinol.* 8: 1289–1297 (1994)). While part of the antiproliferative activities of somatostatin are secondary to its inhibition of hormone and growth factor secretion (e.g., growth hormone and epidermal growth factor), other antiproliferative effects of somatostatin are due to a direct effect on the target cells. As an example, somatostatin analogs inhibit the growth of pancreatic cancer presumably via stimulation of a single PTPase, or a subset of PTPases, rather than a general activation of PTPase levels in the cells (Liebow et al., *Proc. Natl. Acad. Sci. USA* 86: 2003–2007 (1989); Colas et al., *Eur. J. Biochem.* 207: 1017–1024 (1992)). In a recent study it was found that somatostatin stimulation of somatostatin receptors SSTR1, but not SSTR2, stably expressed in CHO-K1 cells can stimulate PTPase activity and that this stimulation is pertussis toxin-sensitive. Whether the inhibitory effect of somatostatin on hormone and growth factor secretion is caused by a similar stimulation of PTPase activity in hormone producing cells remains to be determined.

PTPases: the immune system/autoimmunity

Several studies suggest that the receptor-type PTPase CD45 plays a critical role not only for initiation of T cell activation, but also for maintaining the T cell receptor-mediated signalling cascade. These studies are reviewed in: (Weiss A., *Ann. Rev. Genet.* 25: 487–510(1991); Chan et al., *Annu. Rev. Immunol.* 12: 555–592 (1994); Trowbridge and Thomas, *Annu. Rev. Immunol.* 12: 85–116 (1994)).

CD45 is one of the most abundant of the cell surface glycoproteins and is expressed exclusively on hemopoetic cells. In T cells, it has been shown that CD45 is one of the critical components of the signal transduction machinery of lymphocytes. In particular, evidence has suggested that CD45 phosphatase plays a pivotal role in antigen-stimulated proliferation of T lymphocytes after an antigen has bound to the T cell receptor (Trowbridge, *Ann. Rev. Immunol*, 12:85–116 (1994)). Several studies suggest that the PTPase activity of CD45 plays a role in the activation of Lck, a lymphocyte-specific member of the Src family protein-tyrosine kinase (Mustelin et al., Proc. Natl. Acad. Sci. USA 86: 6302–6306 (1989); Ostergaard et al., Proc. Natl. Acad. Sci. USA 86: 8959–8963 (1989)). These authors hypothesized that the phosphatase activity of CD45 activates Lck by dephosphorylation of a C-terminal tyrosine residue, which may, in turn, be related to T-cell activation. In a recent study it was found that recombinant p56lck specifically associates with recombinant CD45 cytoplasmic domain protein, but not to the cytoplasmic domain of the related PTPa (Ng et al., *J. Biol. Chem.* 271: 1295–1300 (1996)). The p56lck-CD45 interaction seems to be mediated via a non-conventional SH2 domain interaction not requiring phosphotyrosine. In immature B cells, another member of the Src family protein-tyrosine kinases, Fyn, seems to be a selective substrate for CD45 compared to Lck and Syk (Katagiri et al., *J. Biol. Chem.* 270: 27987–27990 (1995)).

Studies using transgenic mice with a mutation for the CD45-exon6 exhibited lacked mature T cells. These mice did not respond to an antigenic challenge with the typical T cell mediated response (Kishihara et al., *Cell* 74:143–56 (1993)). Inhibitors of CD45 phosphatase would therefore be very effective therapeutic agents in conditions that are associated with autoimmune disease.

CD45 has also been shown to be essential for the antibody mediated degranulation of mast cells (Berger et al., *J. Exp. Med.* 180:471–6 (1994)). These studies were also done with mice that were CD45-deficient. In this case, an IgE-mediated degranulation was demonstrated in wild type but not CD45-deficient T cells from mice. These data suggest that CD45 inhibitors could also play a role in the symptomatic or therapeutic treatment of allergic disorders.

Another recently discovered PTPase, an inducible lymphoid-specific protein tyrosine phosphatase (HePTP) has also been implicated in the immune response. This phosphatase is expressed in both resting T and B lymphocytes, but not non-hemopoetic cells. Upon stimulation of these cells, mRNA levels from the HePTP gene increase 10–15 fold (Zanke et al., *Eur. J. Immunol.* 22:235–239 (1992)). In both T and B cells HePTP may function during sustained stimulation to modulate the immune response through dephosphorylation of specific residues. Its exact role, however remains to be defined.

Likewise, the hematopoietic cell specific PTP1C seems to act as a negative regulator and play an essential role in immune cell development. In accordance with the above-mentioned important function of CD45, HePTP and PTP1C, selective PTPase inhibitors may be attractive drug candidates both as immunosuppressors and as immunostimulants. One recent study illustrates the potential of PTPase inhibitors as immunmodulators by demonstrating the capacity of the vanadium-based PTPase inhibitor, BMLOV, to induce apparent B cell selective apoptosis compared to T cells (Schieven et al., *J. Biol. Chem.* 270: 20824–20831 (1995)).

PTPases: cell-cell interactions/cancer

Focal adhesion plaques, an in vitro phenomenon in which specific contact points are formed when fibroblasts grow on appropriate substrates, seem to mimic, at least in part, cells and their natural surroundings. Several focal adhesion proteins are phosphorylated on tyrosine residues when fibroblasts adhere to and spread on extracellular matrix (Gumbiner, *Neuron* 11, 551–564 (1993)). However, aberrant tyrosine phosphorylation of these proteins can lead to cellular transformation. The intimate association between PTPases and focal adhesions is supported by the finding of several intracellular PTPases with ezrin-like N-terminal domains, e.g., PTPMEG1 (Gu et al., *Proc. Natl. Acad. Sci. USA* 88: 5867–5871 (1991)), PTPH1 (Yang and Tonks, *Proc. Natl. Acad. Sci. USA* 88: 5949–5953 (1991)) and PTPD1 (Meller et al., *Proc. Natl. Acad. Sci. USA* 91: 7477–7481 (1994)). The ezrin-like domain show similarity to several proteins that are believed to act as links between the cell membrane and the cytoskeleton. PTPD1 was found to be phosphorylated by and associated with c-src in vitro and is hypothesized to be involved in the regulation of phosphorylation of focal adhesions (Møller et al., supra).

PTPases may oppose the action of tyrosine kinases, including those responsible for phosphorylation of focal adhesion proteins, and may therefore function as natural inhibitors of transformation. TC-PTP, and especially the truncated form of this enzyme (Cool et al., *Proc. Natl. Acad. Sci. USA* 87: 7280–7284 (1990)), can inhibit the transforming activity of v-erb and v-fms (Lammers et al., *J. Biol. Chem.* 268: 22456–22462 (1993); Zander et al., *Oncogene* 8: 1175–1182 (1993)). Moreover, it was found that transformation by the oncogenic form of the HER2/neu gene was suppressed in NIH 3T3 fribroblasts overexpressing PTP1B (Brown-Shimer et al., *Cancer Res.* 52: 478–482 (1992)).

The expression level of PTP1B was found to be increased in a mammary cell line transformed with neu (Zhay et al., *Cancer Res.* 53: 2272–2278 (1993)). The intimate relationship between tyrosine kinases and PTPases in the development of cancer is further evidenced by the recent finding that PTPε is highly expressed in murine mammary tumors in transgenic mice over-expressing c-neu and v-Ha-ras, but not c-myc or int-2 (Elson and Leder, *J. Biol. Chem.* 270: 26116–26122 (1995)). Further, the human gene encoding PTPg was mapped to 3p21, a chromosomal region which is frequenty deleted in renal and lung carcinomas (LaForgia et al., *Proc. Natl. Acad. Sci. USA* 88: 5036–5040 (1991)).

In this context, it seems significant that PTPases appear to be involved in controlling the growth of fibroblasts. In a recent study it was found that Swiss 3T3 cells harvested at high density contain a membrane-associated PTPase whose activity on an average is 8-fold higher than that of cells harvested at low or medium density (Pallen and Tong, *Proc. Natl. Acad. Sci. USA* 88: 6996–7000 (1991)). It was hypothesized by the authors that density-dependent inhibition of cell growth involves the regulated elevation of the activity of the PTPase(s) in question. In accordance with this view, a novel membrane-bound, receptor-type PTPase, DEP-1, showed enhanced (>=10-fold) expression levels with increasing cell density of WI-38 human embryonic lung fibroblasts and in the AG1518 fibroblast cell line (Östman et al., *Proc. Natl. Acad. Sci. USA* 91: 9680–9684 (1994)).

Two closely related receptor-type PTPases, PTPκ and PTPμ, can mediate homophilic cell-cell interaction when expressed in nor-adherent insect cells, suggesting that these PTPases might have a normal physiological function in cell-to-cell signalling (Gebbink et al., *J. Biol. Chem.* 268: 16101–16104 (1993); Brady-Kalnay et al., *J. Cell Biol.* 122: 961–972 (1993); Sap et al., *Mol. Cell. Biol.* 14: 1–9 (1994)). Interestingly, PTPk and PTPμ do not interact with each other, despite their structural similarity (Zondag et al., *J. Biol. Chem.* 270: 14247–14250 (1995)). From the studies described above it is apparent that PTPases may play an important role in regulating normal cell growth. However, as pointed out above, recent studies indicate that PTPases may also function as positive mediators of intracellular signalling and thereby induce or enhance mitogenic responses. Increased activity of certain PTPases might therefore result in cellular transformation and tumor fornation. Indeed, in one study over-expression of PTPα was found to lead to transformation of rat embryo fibroblasts (Zheng, supra). In addition, a novel PTP, SAP-1, was found to be highly expressed in pancreatic and colorectal cancer cells. SAP-1 is mapped to chromosome 19 region q13.4 and might be related to carcinoembryonic antigen mapped to 19q13.2 (Uchida et al., *J. Biol. Chem.* 269: 12220–12228 (1994)). Further, the dsPTPase, cdc25, dephosphorylates cdc2 at Thr14/Tyr-15 and thereby functions as positive regulator of mitosis (reviewed by Hunter, *Cell* 80: 225–236 (1995)). Inhibitors of specific PTPases are therefore likely to be of significant therapeutic value in the treatment of certain forms of cancer.

PTPases: platelet aggregation

Recent studies indicate that PTPases are centrally involved in platelet aggregation. Agonist-induced platelet activation results in calpain-catalyzed cleavage of PTP1B with a concomitant 2-fold stimulation of PTPase activity (Frangioni et al., *EMBO J.* 12: 4843–4856 (1993)). The cleavage of PTP1B leads to subcellular relocation of the enzyme and correlates with the transition from reversible to irreversible platelet aggregation in platelet-rich plasma. In addition, the SH2 domain containing PTPase, SHP-1, was found to translocate to the cytoskeleton in platelets after thrombin stimulation in an aggregation-dependent manner (Li et al., *FEBS Lett.* 343: 89–93 (1994)).

Although some details in the above two studies were recently questioned there is over-all agreement that PTP1B and SHP-1 play significant functional roles in platelet aggregation (Ezumi et al., *J. Biol. Chem.* 270: 11927–11934 (1995)). In accordance with these observations, treatment of platelets with the PTPase inhibitor pervanadate leads to significant increase in tyrosine phosphorylation, secretion and aggregation (Pumiglia et al., *Biochem. J*. 286: 441–449 (1992)).

PTPases: osteoporosis

The rate of bone formation is determined by the number and the activity of osteoblasts, which in term are determined by the rate of proliferation and differentiation of osteoblast progenitor cells, respectively. Histomorphometric studies indicate that the osteoblast number is the primary determinant of the rate of bone formation in humans (Gruber et al., *Mineral Electrolyte Metab.* 12: 246–254 (1987); reviewed in Lau et al., *Biochem. J.* 257: 23–36 (1989)). Acid phosphatases/PTPases may be involved in negative regulation of osteoblast proliferation. Thus, fluoride, which has phosphatase inhibitory activity, has been found to increase spinal bone density in osteoporotics by increasing osteoblast proliferation (Lau et al., supra). Consistent with this observation, an osteoblastic acid phosphatase with PTPase activity was found to be highly sensitive to mitogenic concentrations of fluoride (Lau et al., *J. Biol. Chem.* 260: 4653–4660 (1985); Lau et al., *J. Biol. Chem.* 262: 1389–1397 (1987); Lau et al., *Adv. Protein Phosphatases* 4: 165–198 (1987)). Interestingly, it was recently found that the level of membrane-bound PTPase activity was increased dramatically when the osteoblast-like cell line UMR 106.06 was grown on collagen type-I matrix compared to uncoated tissue culture plates. Since a significant increase in PTPase activity was observed in density-dependent growth arrested fibroblasts (Pallen and Tong, *Proc. Natl. Acad. Sci.* 88: 6996–7000 (1991)), it might be speculated that the increased PTPase activity directly inhibits cell growth. The mitogenic action of fluoride and other phosphatase inhibitors (molybdate and vanadate) may thus be explained by their inhibition of acid phosphatases/PTPases that negatively regulate the cell proliferation of osteoblasts. The complex nature of the involvement of PTPases in bone formation is further suggested by the recent identification of a novel parathyroid regulated, receptor-like PTPase, OST-PTP, expressed in bone and testis (Mauro et al., *J. Biol. Chem.* 269: 30659–30667 (1994)). OST-PTP is up-regulated following differentiation and matrix formation of primary osteoblasts and subsequently down-regulated in the osteoblasts which are actively mineralizing bone in culture. It may be hypothesized that PTPase inhibitors may prevent differentiation via inhibition of OST-PTP or other PTPases thereby leading to continued proliferation. This would be in agreement with the above-mentioned effects of fluoride and the observation that the tyrosine phosphatase inhibitor orthovanadate appears to enhance osteoblast proliferation and matrix formation (Lau et al., *Endocrinology* 116: 2463–2468 (1988)). In addition, it was recently observed that vanadate, vanadyl and pervanadate all increased the growth of the osteoblast-like cell line UMR106. Vanadyl and pervanadate were stronger stimulators of cell growth than vanadate. Only vanadate was able to regulate the cell differentiation as measured by cell alkaline phosphatase activity (Cortizo et al., *Mol. Cell. Biochem.* 145: 97–102 (1995)).

PTPases: microorganisms

Dixon and coworkers have called attention to the fact that PTPases may be a key element in the pathogenic properties of Yersinia (reviewed in Clemens et al. *Molecular Microbiology* 5: 2617–2620 (1991)). This finding was rather surprising since tyrosine phosphate is thought to be absent in bacteria. The genus Yersinia comprises 3 species: *Y. pestis* (responsible for the bubonic plague), *Y. pseudoturberculosis* and *Y. enterocolitica* (causing enteritis and mesenteric lymphadenitis). interestingly, a dual-specificity phosphatase, VH1, has been identified in Vaccinia virus (Guan et al., *Nature* 350: 359–263 (1991)). These observations indicate that PTPases may play critical roles in microbial and parasitic infections, and they further point to PTPase inhibitors as a novel, putative treatment principle of infectious diseases.

SUMMARY OF THE INVENTION

The present invention relates to compounds of formula I, wherein A, $R_1$, $R_2$, $R_3$, $R_4$, $R_{16}$ and $R_{17}$ are as defined in the detailed part of the present description, wherein such compounds are pharmacologically useful inhibitors of Protein Tyrosine Phosphatases (PTPases) such as PTP1B, CD45, SHP-1, SHP-2, PTPα, LAR and HePTP or the like.

The present compounds are useful for the treatment, prevention, elimination, alleviation or amelioration of an indication related to type I diabetes, type II diabetes, impaired glucose tolerance, insulin resistance, obesity, immune dysfunctions including autoimmunity and AIDS, diseases with dysfunctions of the coagulation system, allergic diseases including asthma, osteoporosis, proliferative disorders including cancer and psoriasis, diseases with decreased or increased synthesis or effects of growth hormone, diseases with decreased or increased synthesis of hormones or cytokines that regulate the release of/or response to growth hormone, diseases of the brain including Alzheimers disease and schizophrenia, and infectious diseases.

In another aspect, the present invention includes within its scope pharmaceutical compositions comprising, as an active ingredient, at least one of the compounds of formula I or a pharmaceutically acceptable salt thereof together with a pharmaceutically acceptable carrier or diluent.

In another aspect of the present invention there is provided a method of treating type I diabetes, type II diabetes, impaired glucose tolerance, insulin resistance, obesity, immune dysfunctions including autoimmunity and AIDS, diseases with dysfunctions of the coagulation system, allergic diseases including asthma, osteoporosis, proliferative disorders including cancer and psoriasis, diseases with decreased or increased synthesis or effects of growth hormone, diseases with decreased or increased synthesis of hormones or cytokines that regulate the release of/or response to growth hormone, diseases of the brain including Alzheimer's disease and schizophrenia, and infectious diseases.

The method of treatment may be described as the treatment, prevention, elimination, alleviation or amelioration of one of the above indications, which comprises the step of administering to the said subject a neurologically effective amount of a compound of the invention, or a pharmaceutically acceptable salt thereof.

A further aspect of the invention relates to the use of a compound of the present invention for the preparation of a pharmaceutical composition for the treatment of all type I diabetes, type II diabetes, impaired glucose tolerance, insulin resistance, obesity, immune dysfunctions including autoimmunity and AIDS, diseases with dysfunctions of the coagulation system, allergic diseases including asthma, osteoporosis, proliferative disorders including cancer and psoriasis, diseases with decreased or increased synthesis or effects of growth hormone, diseases with decreased or increased synthesis of hormones or cytokines that regulate the release of/or response to growth hormone, diseases of the brain including Alzheimers disease and schizophrenia, and infectious diseases.

DESCRIPTION OF THE INVENTION

The present invention relates to Compounds of Formula 1 wherein A, $R_1$, $R_2$, $R_3$, $R_4$, $R_{16}$ and $R_{17}$ are defined below;

Formula 1

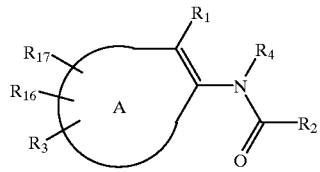

In the above Formula 1

A is together with the double bond in Formula 1 phenyl, biphenyl, indenyl, fluorenyl, fluorenyl-9-one, naphthyl, pyridyl, pyridazinyl, pyrimidyl or pyrazinyl;

$R_1$ is hydrogen, $COR_5$, $OR_6$, $CF_3$, nitro, cyano, $SO_3H$, $SO_2NR_7R_8$, $PO(OH)_2$, $CH_2PO(OH)_2$, $CHFPO(OH)_2$, $CF_2PO(OH)_2$, $C(=NH)NH_2$, $NR_7R_8$ or from the following 5-membered heterocycles:

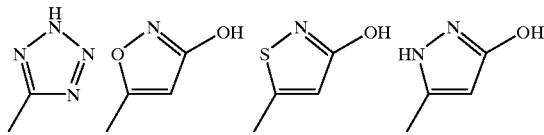

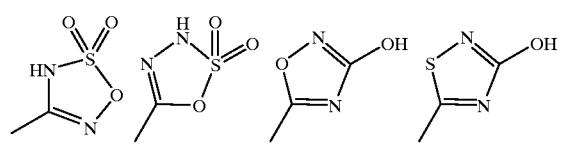

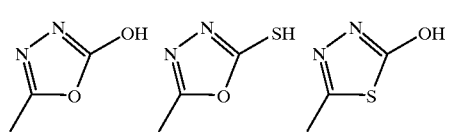

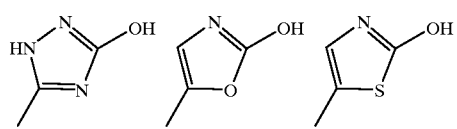

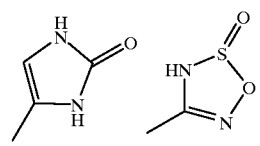

or $R_1$ is

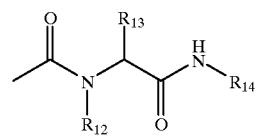

wherein $R_{12}$, $R_{13}$, and $R_{14}$ are independently hydrogen, $C_1$–$C_6$alkyl, aryl, aryl$C_1$–$C_6$alkyl and the alkyl and aryl groups are optionally substituted;

$R_2$ is $COR_5$, $OR_6$, $CF_3$, nitro, cyano, $SO_3H$, $SO_2NR_7R_8$, $PO(OH)_2$, $CH_2PO(OH)_2$, $CHFPO(OH)_2$, $CF_2PO(OH)_2$, $C(=NH)NH_2$, $NR_7R_8$, or selected from the following 5-membered heterocycles:

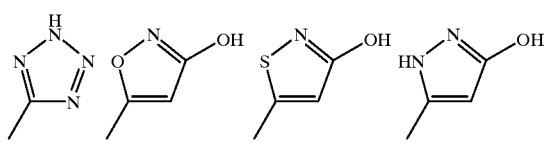

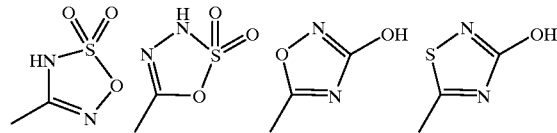

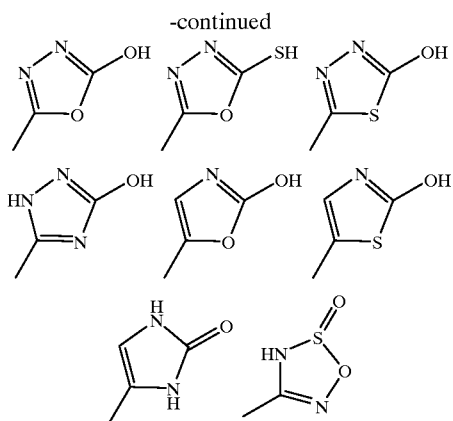

R$_3$, R$_{16}$ and R$_{17}$ are independently hydrogen, halo, nitro, cyano, trihalomethyl, C$_1$–C$_6$alkyl, aryl, arylC$_1$–C$_6$alkyl, hydroxy, carboxy, carboxyC$_1$–C$_6$alkyl, C$_1$–C$_6$alkyloxycarbonyl, aryloxycarbonyl, arylC$_1$–C$_6$alkyloxycarbonyl, C$_1$–C$_6$alkyloxy, C$_1$–C$_6$alkyloxyC$_1$–C$_6$alkyl, aryloxy, arylC$_1$–C$_6$alkyloxy, arylC$_1$–C$_6$alkyloxyC$_1$–C$_6$alkyl, thio, C$_1$–C$_6$alkylthio, C$_1$–C$_6$alkylthioC$_1$–C$_6$alkyl, arylthio, arylC$_1$–C$_6$alkylthio, arylC$_1$–C$_6$alkylthioC$_1$–C$_6$alkyl, NR$_7$R$_8$, C$_1$–C$_6$alkylaminoC$_1$–C$_6$alkyl, arylC$_1$–C$_6$alkylaminoC$_1$–C$_6$alkyl, di(arylC$_1$–C$_6$alkyl)aminoC$_1$–C$_6$alkyl, C$_1$–C$_6$alkylcarbonyl, C$_1$–C$_6$alkylcarbonyl-C$_1$–C$_6$alkyl, arylC$_1$–C$_6$alkylcarbonyl, arylC$_1$–C$_6$alkylcarbonylC$_1$–C$_6$alkyl, C$_1$–C$_6$alkylcarboxy, C$_1$–C$_6$alkylcarboxyC$_1$–C$_6$alkyl, arylcarboxy, arylcarboxyC$_1$–C$_6$alkyl, arylC$_1$–C$_6$alkylcarboxy, arylC$_1$–C$_6$alkylcarboxyC$_1$–C$_6$alkyl, C$_1$–C$_6$alkylcarbonylamino, C$_1$–C$_6$alkylcarbonylaminoC$_1$–C$_6$alkyl, -carbonylNR$_7$C$_1$–C$_6$alkylCOR$_{11}$, arylC$_1$–C$_6$alkylcarbonylamino, arylC$_1$–C$_6$alkylcarbonyl-aminoC$_1$–C$_6$alkyl, CONR$_7$R$_8$, or C$_1$–C$_6$alkylCONR$_7$R$_8$ wherein the alkyl and aryl groups are optionally substituted and R$_{11}$ is NR$_7$R$_8$, or C$_1$–C$_6$alkyl-NR$_7$R$_8$; or R$_3$ is

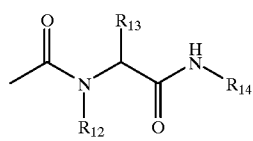

wherein R$_{12}$, R$_{13}$, and R$_{14}$ are independently hydrogen, C$_1$–C$_6$alkyl, aryl, arylC$_1$–C$_6$alkyl and the alkyl and aryl groups are optionally substituted;

R$_4$ is hydrogen, hydroxy, C$_1$–C$_6$alkyl, aryl, arylC$_1$–C$_6$alkyl, NR$_7$R$_8$, C$_1$–C$_6$alkyloxy; wherein the alkyl and aryl groups are optionally substituted;

R$_5$ is hydroxy, C$_1$–C$_6$alkyl, aryl, arylC$_1$–C$_6$alkyl, C$_1$–C$_6$alkyloxy, C$_1$–C$_6$alkyl-oxyC$_1$–C$_6$alkyloxy, aryloxy, arylC$_1$–C$_6$alkyloxy, CF$_3$, NR$_7$R$_8$; wherein the alkyl and aryl groups are optionally substituted;

R$_6$ is hydrogen, C$_1$–C$_6$alkyl, aryl, arylC$_1$–C$_6$alkyl; wherein the alkyl and aryl groups are optionally substituted;

R$_7$ and R$_8$ are independently selected from hydrogen, C$_1$–C$_6$alkyl, aryl, arylC$_1$–C$_6$alkyl, C$_1$–C$_6$alkylcarbonyl, arylcarbonyl, arylC$_1$–C$_6$alkylcarbonyl, C$_1$–C$_6$alkylcarboxy or arylC$_1$–C$_6$alkylcarboxy wherein the alkyl and aryl groups are optionally substituted; or R$_7$ and R$_8$ are together with the nitrogen to which they are attached forming a saturated, partially saturated or aromatic cyclic, bicyclic or tricyclic ring system containing from 3 to 14 carbon atoms and from 0 to 3 additional heteroatoms selected from nitrogen, oxygen or sulfur, the ring system can optionally be substituted with at least one C$_1$–C$_6$alkyl, aryl, arylC$_1$–C$_6$alkyl, hydroxy, oxo, C$_1$–C$_6$alkyloxy, arylC$_1$–C$_6$alkyloxy, C$_1$–C$_6$alkyloxyC$_1$–C$_6$alkyl, NR$_9$R$_{10}$ or C$_1$–C$_6$alkylaminoC$_1$–C$_6$alkyl, wherein R$_9$ and R$_{10}$ are independently selected from hydrogen, C$_1$–C$_6$alkyl, aryl, arylC$_1$–C$_6$alkyl, C$_1$–C$_6$alkylcarbonyl, arylcarbonyl, arylC$_1$–C$_6$alkylcarbonyl, C$_1$–C$_6$alkylcarboxy or arylC$_1$–C$_6$alkylcarboxy; wherein the alkyl and aryl groups are optionally substituted; or R$_7$ and R$_8$ are independently a saturated or partial saturated cyclic 5, 6 or 7 membered amine, imide or lactam; or a salt thereof with a pharmaceutically acceptable acid or base, or any optical isomer or mixture of optical isomers, including a racemic mixture, or any tautomeric forms.

DEFINITIONS

Signal transduction is a collective term used to define all cellular processes that follow the activation of a given cell or tissue. Examples of signal transduction, which are not intended to be in any way limiting to the scope of the invention claimed, are cellular events that are induced by polypeptide hormones and growth factors (e.g. insulin, insulin-like growth factors I and II, growth hormone, epidermal growth factor, platelet-derived growth factor), cytokines (e.g. interleukins), extracellular matrix components, and cell-cell interactions.

Phosphotyrosine recognition units/tyrosine phosphate recognition units/pTyr recognition units are defined as areas or domains of proteins or glycoproteins that have affinity for molecules containing phosphorylated tyrosine residues (pTyr). Examples of pTyr recognition units, which are not intended to be in any way limiting to the scope of the invention claimed, are: PTPases, SH2 domains and PTB domains.

PTPases are defined as enzymes with the capacity to dephosphorylate pTyr-containing proteins or glycoproteins. Examples of PTPases, which are not intended to be in any way limiting to the scope of the invention claimed, are: 'classical' PTPases (intracellular PTPases (e.g. PTP1B, TC-PTP, PTP1C, PTP1D, PTPD1, PTPD2) and receptor-type PTPases (e.g. PTPα, PTPε, PTPβ, PTPγ, CD45, PTPκ, PTPμ), dual specificty phosphatases (VH1, VHR, cdc25), LMW-PTPases or acid phosphatases.

SH2 domains (Src homology 2 domains) are non-catalytic protein modules that bind to pTyr (phosphotyrosine residue) containing proteins, i.e. SH2 domains are pTyr recognition units. SH2 domains, which consist of ~100 amino acid residues, are found in a number of different molecules involved in signal transduction processes. The following is a non-limiting list of proteins containing SH2 domains: Src, Hck, Lck, Syk, Zap70, SHP-1, SHP-2, STATs, Grb-2, Shc, p85/PI3K, Gap, vav (see Russell et al., FEBS Lett. 304:15–20 (1992); Pawson, Nature 373: 573580 (1995); Sawyer, Biopolymers (Peptide Science) 47: 243–261 (1998); and references herein).

As used herein, the term "attached" or "—" (e.g. —$COR_{11}$ which indicates the carbonyl attachment point to the scaffold) signifies a stable covalent bond, certain preferred points of attachment points being apparent to those skilled in the art. The terms "halogen" or "halo" include fluorine, chlorine, bromine, and iodine. The term "alkyl" includes $C_1$–$C_2$ straight chain saturated and $C_2$–$C_6$ unsaturated aliphatic hydrocarbon groups, $C_1$–$C_6$ branched saturated and $C_2$–$C_6$ unsaturated aliphatic hydrocarbon groups, $C_3$–$C_6$ cycic saturated and $C_5$–$C_6$ unsaturated aliphatic hydrocarbon groups, and $C_1$–$C_6$ straight chain or branched saturated and $C_2$–$C_6$ straight chain or branched unsaturated aliphatic hydrocarbon groups substituted with $C_3$–$C_6$ cyclic saturated and unsaturated aliphatic hydrocarbon groups having the specified number of carbon atoms. For example, this definition shall include but is not limited to methyl (Me), ethyl (Et), propyl (Pr), butyl (Bu), pentyl, hexyl, heptyl, ethenyl, propenyl, butenyl, penentyl, hexenyl, isopropyl (i-Pr), isobutyl (i-Bu), tert-butyl (t-Bu), sec-butyl (s-Bu), isopentyl, neopentyl, cyclopropyl, cyclobutyl, cyclopentyl, cyclohexyl, cyclopentenyl, cyclohexenyl, methylcyclopropyl, ethylcyclohexenyl, butenylcyclopentyl, and the like.

The term "substituted alkyl" represents an alkyl group as defined above wherein the substitutents are independently selected from halo, cyano, nitro, trihalomethyl, carbamoyl, hydroxy, oxo, $COR_5$, $C_1$–$C_6$alkyl, $C_1$–$C_6$alkyloxy, aryloxy, aryl$C_1$–$C_6$alkyloxy, thio, $C_1$–$C_6$alkylthio, arylthio, aryl$C_1$–$C_6$alkylthio, $NR_7R_8$, $C_1$–$C_6$alkylamino, arylamino, aryl$C_1$–$C_6$alkylamino, di(aryl$C_1$–$C_6$alkyl)amino, $C_1$–$C_6$alkylcarbonyl, aryl$C_1$–$C_6$alkylcarbonyl, $C_1$–$C_6$alkylcarboxy, arylcarboxy, aryl$C_1$–$C_6$alkylcarboxy, $C_1$–$C_6$alkylcarbonyl-amino, —$C_1$–$C_6$alkylamino$COR_{11}$, aryl$C_1$–$C_6$alkylcarbonylamino, tetrahydrofuranyl, morpholinyl, piperazinyl, —$CONR_7R_8$, —$C_1$–$C_6$alkyl-$CONR_7R_8$, or a saturated or partial saturated cyclic 5, 6 or 7 membered amine, imide or lactam; wherein $R_{11}$ is hydroxy, $C_1$–$C_6$alkyl, aryl, aryl$C_1$–$C_6$alkyl, $C_1$–$C_6$alkyloxy, aryloxy, aryl$C_1$–$C_6$alkyloxy and $R_5$ is defined as above or $NR_7R_8$, wherein $R_7$, $R_8$ are defined as above.

The term "saturated, partially saturated or aromatic cyclic, bicyclic or tricyclic ring system" represents but are not limit to aziridinyl, pyrrolyl, pyrrolinyl, pyrrolidinyl, imidazolyl, 2-imidazolinyl, imidazolidinyl, pyrazolyl, 2-pyrazolinyl, 1,2,3-triazolyl, 1,2,4-triazolyl, morpholinyl, piperidinyl, thiomorpholinyl, piperazinyl, indolyl, isoindolyl, 1,2,3,4-tetrahydro-quinolinyl, 1,2,3,4-tetrahydro-isoquinolinyl, 1,2,3,4-tetrahydro-quinoxalinyl, indolinyl, indazolyl, benzimidazolyl, benzotriazolyl, purinyl, carbazolyl, acridinyl, phenothiazinyl, phenoxazinyl, iminodibenzyl, iminostilbenyl.

The term "alkyloxy" (e.g. methoxy, ethoxy, propyloxy, allyloxy, cyclohexyloxy) represents an "alkyl" group as defined above having the indicated number of carbon atoms attached through an oxygen bridge. The term "alkyloxyalkyl" represents an "alkyloxy" group attached through an alkyl group as defined above having the indicated number of carbon atoms.

The term "alkyloxyalkyloxy" represents an "alkyloxyalkyl" group attached through an oxygen atom as defined above having the indicated number of carbon atoms.

The term "aryloxy" (e.g. phenoxy, naphthyloxy and the like) represents an aryl group as defined below attached through an oxygen bridge.

The term "arylalkyloxy" (e.g. phenethyloxy, naphthylmethyloxy and the like) represents an "arylalkyl" group as defined below attached through an oxygen bridge.

The term "arylalkyloxyalkyl" represents an "arylalkyloxy" group as defined above attached through an "alkyl" group defined above having the indicated number of carbon atoms.

The term "arylthio" (e.g. phenylthio, naphthylthio and the like) represents an "aryl" group as defined below attached through an sulfur bridge.

The term "alkyloxycarbonyl" (e.g. methylformiat, ethylformiat and the like) represents an "alkyloxy" group as defined above attached through a carbonyl group.

The term "aryloxycarbonyl" (e.g. phenylformiat, 2-thiazolylformiat and the like) represents an "aryloxy" group as defined above attached through a carbonyl group. The term "arylalkyloxycarbonyl" (e.g. benzylformiat, phenyletylformiat and the like) represents an "arylalkyloxy" group as defined above attached through a carbonyl group.

The term "alkyloxycarbonylalkyl" represents an "alkyloxycarbonyl" group as defined above attached through an "alkyl" group as defined above having the indicated number of carbon atoms.

The term "arylalkyloxycarbonylalkyl" represents an "arylalkyloxycarbonyl" group as defined above attached through an "alkyl" group as defined above having the indicated number of carbon atoms.

The term "alkylthio" (e.g. methylthio, ethylthio, propylthio, cyclohexenylthio and the like) represents an "alkyl" group as defined above having the indicated number of carbon atoms attached through a sulfur bridge.

The term "arylalkylthio" (e.g. phenylmethylthio, phenylethylthio, and the like) represents an "arylalkyl" group as defined above having the indicated number of carbon atoms attached through a sulfur bridge.

The term "alkylthioalkyl" represents an "alkylthio" group attached through an alkyl group as defined above having the indicated number of carbon atoms.

The term "arylalkylthioalkyl" represents an "arylalkylthio" group attached through an alkyl group as defined above having the indicated number of carbon atoms.

The term "alkylamino" (e.g. methylamino, diethylamino, butylamino, N-propyl-N-hexylamino, (2-cyclopentyl)propylamino, hexenylamino, pyrrolidinyl, piperidinyl and the like) represents one or two "alkyl" groups as defined above having the indicated number of carbon atoms attached through an amine bridge. The two alkyl groups may be taken together with the nitrogen to which they are attached forming a saturated, partially saturated or aromatic cyclic, bicyclic or tricyclic ring system containing from 3 to 14 carbon atoms and from 0 to 3 additional heteroatoms selected from nitrogen, oxygen or sulfur, the ring system can optionally be substituted with at least one $C_1$–$C_6$alkyl, aryl, aryl$C_1$–$C_6$alkyl, hydroxy, oxo, $C_1$–$C_6$alkyloxy, aryl$C_1$–$C_6$alkyloxy, $C_1$–$C_6$alkyloxy$C_1$–$C_6$alkyl, $NR_9R_{10}$ or $C_1$–$C_6$alkylamino$C_1$–$C_6$alkyl substituent wherein the alkyl and aryl groups are optionally substituted as defined in the definition section and $R_9$ and $R_{10}$ are defined as above.

The term "arylalkylamino" (e.g. benzylamino, diphenylethylamino and the like) represents one or two "arylalkyl" groups as defined above having the indicated number of carbon atoms attached through an amine bridge. The two "arylalkyl" groups may be taken together with the nitrogen to which they are attached forming a saturated, partially saturated or aromatic cyclic, bicyclic or tricyclic ring system containing from 3 to 14 carbon atoms and from 0 to 3 additional heteroatoms selected from nitrogen, oxygen or sulfur, the ring system can optionally be substituted with at least one $C_1$–$C_6$alkyl, aryl, aryl$C_1$–$C_6$alkyl, hydroxy, oxo, $C_1$–$C_6$alkyloxy, aryl$C_1$–$C_6$alkyloxy, $C_1$–$C_6$alkyloxy$C_1$–$C_6$alkyl, $NR_9R_{10}$ or $C_1$–$C_6$alkylamino$C_1$–$C_6$alkyl substituent wherein the alkyl and aryl groups are optionally substituted as defined in the definition section and $R_9$ and $R_{10}$ are defined as above.

The term "alkylaminoalkyl" represents an "alkylamino" group attached through an alkyl group as defined above having the indicated number of carbon atoms.

The term "arylalkylaminoalkyl" represents an "arylalkylamino" group attached through an alkyl group as defined above having the indicated number of carbon atoms.

The term "arylalkyl" (e.g. benzyl, phenylethyl) represents an "aryl" group as defined below attached through an alkyl having the indicated number of carbon atoms or substituted alkyl group as defined above.

The term "alkylcarbonyl" (e.g. cyclooctylcarbonyl, pentylcarbonyl, 3-hexenylcarbonyl) represents an "alkyl" group as defined above having the indicated number of carbon atoms attached through a carbonyl group.

The term "arylcarbonyl" (benzoyl) represents an "aryl" group as defined above attached through a carbonyl group.

The term "arylalkylcarbonyl" (e.g. phenylcyclopropylcarbonyl, phenylethylcarbonyl and the like) represents an "arylalkyl" group as defined above having the indicated number of carbon atoms attached through a carbonyl group.

The term "alkylcarbonylalkyl" represents an "alkylcarbonyl" group attached through an "alkyl" group as defined above having the indicated number of carbon atoms.

The term "arylalkylcarbonylalkyl" represents an "arylalkylcarbonyl" group attached through an alkyl group as defined above having the indicated number of carbon atoms.

The term "alkylcarboxy" (e.g. heptylcarboxy, cyclopropylcarboxy, 3-pentenylcarboxy) represents an "alkylcarbonyl" group as defined above wherein the carbonyl is in turn attached through an oxygen bridge.

The term "arylalkylcarboxy" (e.g. benzylcarboxy, phenylcyclopropylcarboxy and the like) represents an "arylalkylcarbonyl" group as defined above wherein the carbonyl is in turn attached through an oxygen bridge.

The term "arylcarboxyalkyl" (e.g. phenylcarboxymethyl) represents an "arylcarbonyl" group defined above wherein the carbonyl is in turn attached through an oxygen bridge to an alkyl chain having the indicated number of carbon atoms.

The term "alkylcarboxyalkyl" represents an "alkylcarboxy" group attached through an "alkyl" group as defined above having the indicated number of carbon atoms.

The term "arylalkylcarboxyalkyl" represents an "arylalkylcarboxy" group attached through an "alkyl" group as defined above having the indicated number of carbon atoms.

The term "alkylcarbonylamino" (e.g. hexylcarbonylamino, cyclopentylcarbonylaminomethyl, methylcarbonylaminophenyl) represents an "alkylcarbonyl" group as defined above wherein the carbonyl is in turn attached through the nitrogen atom of an amino group. The nitrogen atom may itself be substituted with an alkyl or aryl group.

The term "arylalkylcarbonylamino" (e.g. benzylcarbonylamino and the like) represents an "arylalkylcarbonyl" group as defined above wherein the carbonyl is in turn attached through the nitrogen atom of an amino group. The nitrogen atom may itself be substituted with an alkyl or aryl group.

The term "alkylcarbonylaminoalkyl" represents an "alkylcarbonylamino" group attached through an "alkyl" group as defined above having the indicated number of carbon atoms. The nitrogen atom may itself be substituted with an alkyl or aryl group.

The term "arylalkylcarbonylaminoalkyl" represents an "arylalkylcarbonylamino" group attached through an "alkyl" group as defined above having the indicated number of carbon atoms. The nitrogen atom may itself be substituted with an alkyl or aryl group.

The term "alkylcarbonylaminoalkylcarbonyl" represents an alkylcarbonylaminoalkyl group attached through a carbonyl group. The nitrogen atom may be further substituted with an "alkyl" or "aryl" group.

The term "aryl" represents an unsubstituted, mono-, di- or trisubstituted monocyclic, polycyclic, biaryl and heterocyclic aromatic groups covalently attached at any ring position capable of forming a stable covalent bond, certain preferred points of attachment being apparent to those skilled in the art (e.g., 3-indolyl, 4-imidazolyl). The aryl substituents are independently selected from the group consisting of halo, nitro, cyano, trihalomethyl, $C_1$–$C_6$alkyl, aryl, aryl$C_1$–$C_6$alkyl, hydroxy, $COR_5$, $C_1$–$C_6$alkyloxy, $C_1$–$C_6$alkyloxy$C_1$–$C_6$alkyl, aryloxy, aryl$C_1$–$C_6$alkyloxy, aryl$C_1$–$C_6$alkyloxy$C_1$–$C_6$alkyl, thio, $C_1$–$C_6$alkylthio, $C_1$–$C_6$alkylthio$C_1$–$C_6$alkyl, arylthio, aryl$C_1$–$C_6$alkylthio, aryl$C_1$–$C_6$alkylthio$C_1$–$C_6$alkyl, $NR_8R_9$, $C_1$–$C_6$alkylamino, $C_1$–$C_6$alkylamino$C_1$–$C_6$alkyl, arylamino, aryl$C_1$–$C_6$alkylamino, aryl$C_1$–$C_6$alkyl-amino$C_1$–$C_6$alkyl, di(aryl$C_1$–$C_6$alkyl)amino$C_1$–$C_6$alkyl, $C_1$–$C_6$alkylcarbonyl, $C_1$–$C_6$alkylcarbonyl$C_1$–$C_6$alkyl, aryl$C_1$–$C_6$alkylcarbonyl, aryl$C_1$–$C_6$alkyl-carbonyl$C_1$–$C_6$alkyl, $C_1$–$C_6$alkylcarboxy, $C_1$–$C_6$alkylcarboxy$C_1$–$C_6$alkyl, aryl$C_1$–$C_6$alkylcarboxy, aryl$C_1$–$C_6$alkylcarboxy$C_1$–$C_6$alkyl, carboxy$C_1$–$C_6$alkyloxy, $C_1$–$C_6$alkylcarbonylamino, $C_1$–$C_6$alkylcarbonylamino$C_1$–$C_6$alkyl, -carbonyl$NR_7C_1$–$C_6$alkyl$COR_{11}$, aryl$C_1$–$C_6$alkylcarbonyl-amino, aryl$C_1$–$C_6$alkylcarbonylamino$C_1$–$C_6$alkyl, —$CONR_8R_9$, or —$C_1$–$C_6$alkyl-$CONR_8R_9$; wherein $R_7$, $R_8$, $R_9$, and $R_{11}$ are defined as above and the alkyl and aryl groups are optionally substituted as defined in the definition section.

The definition of aryl includes but is not limited to phenyl, biphenyl, indenyl, fluorenyl, naphthyl (1-naphthyl, 2-naphthyl), pyrrolyl (2-pyrrolyl), pyrazolyl (3-pyrazolyl), imidazolyl (1-imidazolyl, 2-imidazolyl, 4-imidazolyl, 5-imidazolyl), triazolyl (1,2,3-triazol-1-yl, 1,2,3-triazol-2-yl 1,2,3triazol-4-yl, 1,2,4-triazol-3-yl), oxazolyl (2-oxazolyl, 4-oxazolyl, 5-oxazolyl), isoxazolyl (3-isoxazolyl, 4-isoxazolyl, 5-isoxazolyl), thiazolyl (2-thiazolyl, 4-thiazolyl, 5-thiazolyl), thiophenyl (2-thiophenyl, 3-thiophenyl, 4-thiophenyl, 5-thiophenyl), furanyl (2-furanyl, 3-furanyl, 4-furanyl, 5-furanyl), pyridyl (2-pyndyl, 3-pyridyl, 4-pyridyl, 5-pyridyl), 5-tetrazolyl, pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl (2-(2,3-dihydro-benzo[b]furanyl), 3-(2,3-dihydro-benzo[b]furanyl), 4-(2,3-dihydro-benzo[b]furanyl), 5-(2,3-dihydro-benzo-[b]furanyl), 6-(2,3-dihydro-benzo-[b]furanyl), 7-(2,3-dihydro-benzo[b]furanyl)), benzo[b]thiophenyl (2-benzo[b]thiophenyl, 3-benzo[b]thiophenyl, 4-benzo[b]thiophenyl, 5-benzo[blthiophenyl, 6-benzofb]thiophenyl, 7-benzo[b]thiophenyl), 2,3-dihydro-benzo[b]

thiophenyl (2-(2,3-dihydro-benzo[b]thiophenyl), 3-(2,3-dihydro-benzo[b]4hiophenyl), 4-(2,3-dihydro-benzo[b]thiophenyl), 5-(2,3-dihydro-benzo[b]-thiophenyl), 6-(2,3-dihydro-benzo[b]thiophenyl), 7-(2,3-dihydro-benzo[b]-thiophenyl)), 4,5,6,7-tetrahydro-benzo[b]thiophenyl (2-(4,5,6,7-tetrahydro-benzo-[b]thiophenyl), 3-(4,5,6,7-tetrahydro-benzo-[b]thiophenyl), 4-(4,5,6,7-tetrahydro-benzo[b]thiophenyl), 5-(4,5,6,7-tetrahydro-benzo-[b]thiophenyl), 6-(4,5,6,7-tetrahydro-benzo-[b]thiophenyl), 7-(4,5,6,7-tetrahydro-benzo[b]thiophenyl)), 4,5,6,7-tetrahydro-thieno[2,3-c]pyridyl (4-(4,5,6,7-tetrahydro-thieno[2,3-c]pyridyl), 5-4,5,6,7-tetrahydro-thieno[2,3-c]pyridyl), 6-(4,5,6,7-tetrahydro-thieno[2,3-c]pyridyl), 7-(4,5,6,7-tetrahydro-thieno[2,3-c]pyridyl)), indolyl (1-indolyl, 2-indolyl, 3-indolyl, 4-indolyl, 5-indolyl, 6-indolyl, 7-indolyl), isoindolyl (1-isoindolyl, 2-isoindolyl, 3-isoindolyl, 4-isoindolyl, 5-isoindolyl, 6-isoindolyl, 7-isoindolyl), 1,3-dihydro-isoindolyl (1-(1,3-dihydro-isoindolyl), 2-(1,3-dihydro-isoindolyl), 3-(1,3-dihydro-isoindolyl), 4-(1,3-dihydro-isoindolyl), 5-(1,3-dihydro-isoindolyl), 6-(1,3-dihydro-isoindolyl), 7-(1,3-dihydro-isoindolyl)), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benz-oxazolyl, 2-benzoxazolyl), benzothiazolyl (1-benzothiazolyl, 2-benzo-thiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl), 5H-dibenz[b,f]azepine (5H-dibenz[b,f]azepin-1-yl, 5H-dibenz-[b,f]azepine-2-yl, 5H-dibenz[b,f]azepine-3-yl, 5H-dibenz-[b,f]azepine-4-yl, 5H-dibenz[b,f]-azepine-5-yl), 10,11-dihydro-5H-dibenz[b,f]azepine (10,11-dihydro-5H-dibenz[b,f]azepine-1-yl, 10,11-dihydro-5H-dibenz[b,f]azepine-2-yl, 10,11-dihydro-5H-dibenz[b,f]azepine-3-yl, 10,11-dihydro-5H-dibenz-[b,f]azepine-4-yl, 10,11-dihydro-5H-dibenz[b,f]azepine-5-yl), piperidinyl (2-piperidinyl, 3-piperidinyl, 4-piperidinyl), pyrrolidinyl (1-pyrrolidinyl, 2-pyrrolidinyl, 3-pyrrolidinyl), phenylpyridyl (2-phenyl-pyridyl, 3-phenyl-pyridyl, 4-phenylpyridyl), phenylpyrimidinyl (2-phenylpyrimidinyl, 4-phenyl-pyrimidinyl, 5-phenylpyrimidinyl, 6-phenylpyrimidinyl), phenylpyrazinyl, phenylpyridazinyl (3-phenylpyridazinyl, 4-phenylpyridazinyl, 5-phenyl-pyridazinyl).

The term "arylcarbonyl" (e.g. 2-thiophenylcarbonyl, 3-methoxy-anthrylcarbonyl, oxazolylcarbonyl) represents an "aryl" group as defined above attached through a carbonyl group.

The term "arylalkylcarbonyl" (e.g. (2,3-dimethoxyphenyl)-propylcarbonyl, (2-chloronaphthyl)pentenylcarbonyl, imidazolylcyclo-pentylcarbonyl) represents an "arylalkyl" group as defined above wherein the "alkyl" group is in turn attached through a carbonyl.

The compounds of the present invention have asymmetric centers and may occur as racemates, racemic mixtures, and as individual enantiomers or diastereoisomers, with all isomeric forms being included in the present invention as well as mixtures thereof.

Pharmaceutically acceptable salts of the compounds of formula 1, where a basic or acidic group is present in the structure, are also included within the scope of this invention. When an acidic substituent is present, such as —COOH, 5-tetrazolyl or —P(O)(OH)$_2$, there can be formed the ammonium, morpholinium, sodium, potassium, barium, calcium salt, and the like, for use as the dosage form. When a basic group is present, such as amino or a basic heteroaryl radical, such as pyridyl, an acidic salt, such as hydrochloride, hydrobromide, phosphate, sulfate, trifluoroacetate, trichloroacetate, acetate, oxalate, maleate, pyruvate, malonate, succinate, citrate, tartarate, fumarate, mandelate, benzoate, cinnamate, methanesulfonate, ethane sulfonate, picrate and the like, and include acids related to the pharmaceutically acceptable salts listed in Journal of Pharmaceutical Science, 66, 2 (1977) and incorporated herein by reference, can be used as the dosage form.

Also, in the case of the —COOH or —P(O)(OH)$_2$ being present, pharmaceutically acceptable esters can be employed, e.g., methyl, tert-butyl, acetoxymethyl, pivaloyloxymethyl, and the like, and those esters known in the art for modifying solubility or hydrolysis characteristics for use as sustained release or prodrug formulations.

In addition, some of the compounds of the instant invention may form solvates with water or common organic solvents. Such solvates are encompassed within the scope of the invention.

The term "therapeutically effective amount" shall mean that amount of drug or pharmaceutical agent that will elicit the biological or medical response of a tissue, system, animal, or human that is being sought by a researcher, veterinarian, medical doctor or other.

PREFERRED EMBODIMENTS OF THE INVENTION

Compounds of Formula 1a are preferred compounds of the invention

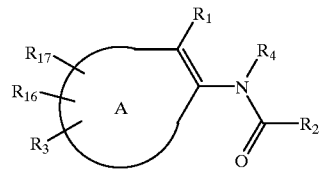

Formula 1a wherein

A is together with the double bond in Formula 1a phenyl, biphenyl, indenyl, fluorenyl, fluorenyl-9-one or naphthyl;

$R_1$ is $COR_5$, $OR_6$, $CF_3$, nitro, cyano, $SO_3H$, $SO_2NR_7R_8$, $PO(OH)_2$, $CH_2PO(OH)_2$ $CHFPO(OH)_2$, $CF_2PO(OH)_2$, $C(=NH)NH_2$, $NR_7R_8$ or selected from the following 5-membered heterocycles:

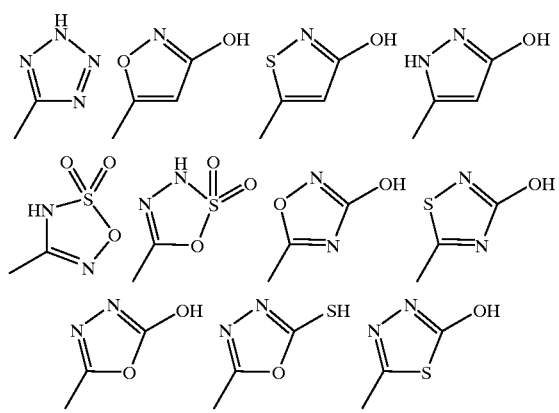

-continued

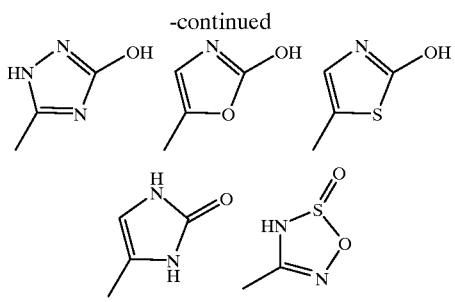

or R₁ is

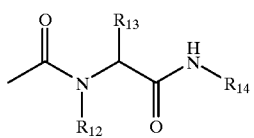

wherein $R_{12}$, $R_{13}$, and $R_{14}$ are independently hydrogen, $C_1–C_6$alkyl, aryl, aryl$C_1–C_6$alkyl and the alkyl and aryl groups are optionally substituted;

$R_2$ is $COR_5$, $OR_6$, $CF_3$, nitro, cyano, $SO_3H$, $SO_2NR_7R_8$, $PO(OH)_2$, $CH_2PO(OH)_2$, $CHFPO(OH)_2$, $CF_2PO(OH)_2$, $C(=NH)NH_2$, $NR_7R_8$, or selected from the following 5-membranes heterocycles:

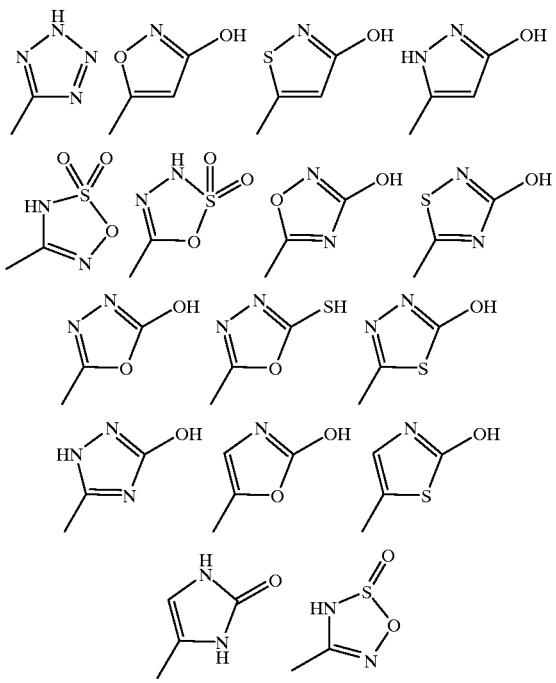

$R_3$, $R_{16}$ and $R_{17}$ are independently hydrogen, halo, nitro, cyano, trihalomethyl, $C_1–C_6$alkyl, aryl, aryl$C_1–C_6$-alkyl, hydroxy, carboxy, carboxy$C_1–C_6$alkyl, $C_1–C_6$alkyloxy-carbonyl, aryloxycarbonyl, aryl$C_1–C_6$alkyloxycarbonyl, $C_1–C_6$alkyloxy, $C_1–C_6$alkyl-oxy$C_1–C_6$alkyl, aryloxy, aryl$C_1–C_6$alkyloxy, aryl$C_1–C_6$alkyl-oxy$C_1–C_6$alkyl, thio, $C_1–C_6$alkylthio, $C_1–C_6$alkylthio$C_1–C_6$alkyl, arylthio, aryl$C_1–C_6$alkylthio, aryl$C_1–C_6$alkylthio$C_1–C_6$alkyl, $NR_7R_8$, $C_1–C_6$alkyl-amino$C_1–C_6$alkyl, aryl$C_1–C_6$alkylamino$C_1–C_6$alkyl, di(aryl$C_1–C_6$alkyl)-amino$C_1–C_6$alkyl, $C_1–C_6$alkylcarbonyl, $C_1–C_6$alkylcarbonyl$C_1–C_6$alkyl, aryl$C_{1–C6}$alkylcarbonyl, aryl$C_1–C_6$alkylcarbonyl$C_1–C_6$alkyl, $C_1–C_6$alkyl-carboxy, $C_1–C_6$alkyl-carboxy$C_1–C_6$-alkyl, arylcarboxy, aryl$C_1–C_6$alkylcarboxy, aryl$C_1–C_6$alkylcarboxy$C_1–C_6$alkyl, $C_1–C_6$alkylcarbonylamino, $C_1–C_6$alkylcarbonyl-amino$C_1–C_6$alkyl, -carbonyl$NR_7C_1–C_6$alkyl$COR_{11}$, aryl$C_1–C_6$alkyl-carbonylamino, aryl$C_1–C_6$alkylcarbonylamino$C_1–C_6$alkyl, $CONR_7R_8$, or $C_1–C_6$alkyl$CONR_7R_8$ wherein the alkyl and aryl groups are optionally substituted and $R_{11}$, is $NR_7R_8$, or $C_1–C_6$alkyl$NR_7R_8$; or $R_3$ is

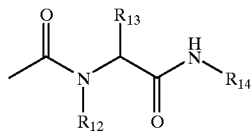

wherein $R_{12}$, $R_{13}$, and $R_{14}$ are independently hydrogen, $C_1–C_6$alkyl, aryl, aryl$C_1–C_6$alkyl and the alkyl and aryl groups are optionally substituted;

$R_4$ is hydrogen, hydroxy, $C_1–C_6$alkyl, aryl, aryl$C_1–C_6$alkyl, $NR_7R_8$, $C_1–C_6$alkyloxy; wherein the alkyl and aryl groups are optionally substituted;

$R_5$ is hydroxy, $C_1–C_6$alkyl, aryl, aryl$C_1–C_6$alkyl, $CF_3$, $NR_7R_8$; wherein the alkyl and aryl groups are optionally substituted;

$R_6$ is hydrogen, $C_1–C_6$alkyl, aryl, aryl$C_1–C_6$alkyl; wherein the alkyl and aryl groups are optionally substituted;

$R_7$ and $R_8$ are independently selected from hydrogen, $C_1–C_6$alkyl, aryl, aryl$C_1–C_6$alkyl, $C_1–C_6$alkyl-carbonyl, arylcarbonyl, aryl$C_1–C_6$alkyl-carbonyl, $C_1–C_6$alkyl-carboxy or aryl$C_1–C_6$alkylcarboxy wherein the alkyl and aryl groups are optionally substituted; or $R_7$ and $R_8$ are taken together with the nitrogen to which they are attached forming a cyclic or bicyclic system containing 3 to 11 carbon atoms and 0 to 2 additional heteroatoms selected from nitrogen, oxygen or sulfur, the ring system can optionally be substituted with at least one $C_1–C_6$alkyl, aryl, aryl$C_1–C_6$alkyl, hydroxy, $C_1–C_6$alkyloxy, aryl$C_1–C_6$alkyloxy, $C_1–C_6$alkyloxy$C_1–C_6$alkyl, $NR_9R_{10}$ or $C_1–C_6$alkylamino-$C_1–C_6$alkyl, wherein $R_9$ and $R_{10}$ are independently selected from hydrogen, $C_1–C_6$alkyl, aryl, aryl$C_1–C_6$alkyl, $C_1–C_6$alkylcarbonyl, arylcarbonyl, aryl$C_1–C_6$alkylcarbonyl, $C_1–C_6$alkyl-carboxy or aryl$C_1–C_6$alkylcarboxy; wherein the alkyl and aryl groups are optionally substituted; or $R_7$ and $R_8$ are independently a saturated or partially saturated cyclic 5, 6 or 7 membered amine or lactam;

or a salt thereof with a pharmaceutically acceptable acid or base, or any optical isomer or mixture of optical isomers, including a racemic mixture, or any tautomeric forms.

Also, compounds of Formula 1c are preferred compounds of the invention

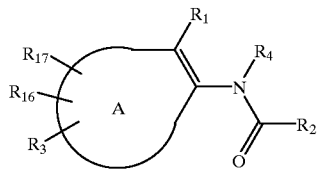

Formula 1c wherein A is together with the double bond in Formula 1c pyridyl, pyridazinyl, pyrimidyl or pyrazinyl;

$R_1$ is $COR_5$, $OR_6$, $CF_3$, nitro, cyano, $SO_3H$, $SO_2NR_7R_8$, $PO(OH)_2$, $CH_2PO(OH)_{CHFPO(OH)2}$, $CF_2PO(OH)_2$, $C(=NH)NH_2$, $NR_7R_8$ or selected from the following 5-membered heterocycles:

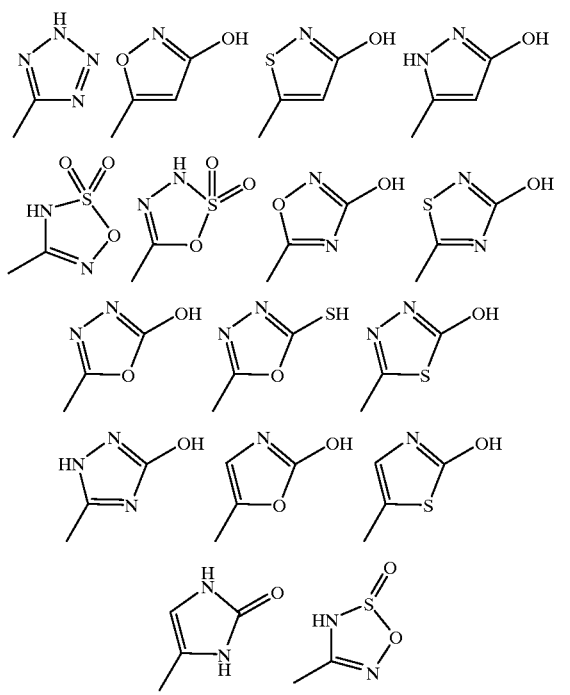

or $R_1$ is

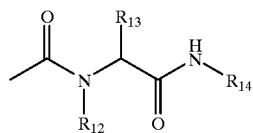

wherein $R_{12}$, $R_{13}$, and $R_{14}$ are independently hydrogen, $C_1$–$C_6$alkyl, aryl, aryl$C_1$–$C_6$alkyl and the alkyl and aryl groups are optionally substituted;

$R_2$ is $COR_5$, $OR_6$, $CF_3$, nitro, cyano, $SO_3H$, $SO_2NR_7R_8$, $PO(OH)_2$, $CH_2PO(OH)_2$, $CHFPO(OH)_2$, $CF_2PO(OH)_2$, $C(=NH)NH_2$, $NR_7R_8$, or selected from the following 5-membered heterocycles:

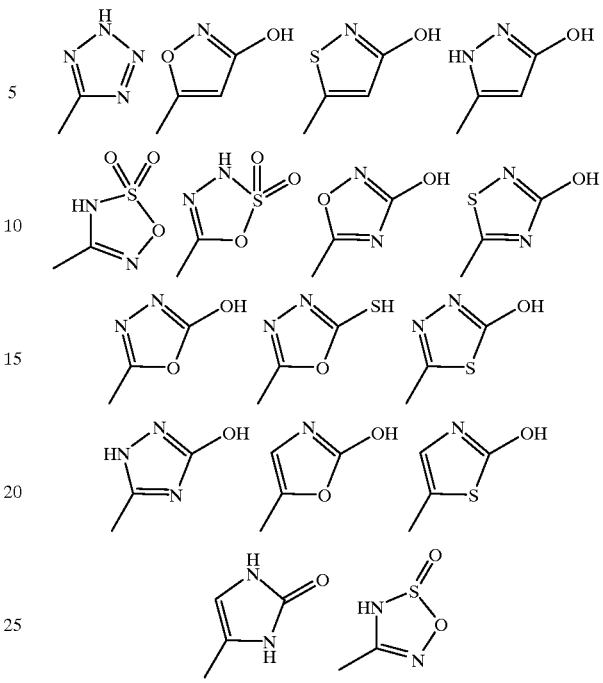

$R_3$, $R_{16}$ and $R_{17}$ are independently hydrogen, halo, nitro, cyano, trihalomethyl, $C_1$–$C_6$alkyl, aryl, aryl$C_1$–$C_6$-alkyl, hydroxy, carboxy, carboxy$C_1$–$C_6$alkyl, $C_1$–$C_6$alkyloxy-carbonyl, aryloxycarbonyl, aryl$C_1$–$C_6$alkyloxycarbonyl, $C_1$–$C_6$alkyloxy, $C_1$–$C_6$alkyl-oxy$C_1$–$C_6$alkyl, aryloxy, aryl$C_1$–$C_6$alkyloxy, aryl$C_1$–$C_6$alkyl-oxy$C_1$–$C_6$alkyl, thio, $C_1$–$C_6$alkylthio, $C_1$–$C_6$alkylthio$C_1$–$C_6$alkyl, arylthio, aryl$C_1$–$C_6$alkylthio, aryl$C_1$–$C_6$alkylthio$C_1$–$C_6$alkyl, $NR_7R_8$, $C_1$–$C_6$alkyl-amino$C_1$–$C_6$alkyl, aryl$C_1$–$C_6$alkylamino$C_1$–$C_6$alkyl, di(aryl$C_1$–$C_6$alkyl)-amino$C_1$–$C_6$alkyl, $C_1$–$C_6$alkylcarbonyl, $C_1$–$C_6$alkylcarbonyl$C_1$–$C_6$alkyl, aryl$C_1$–$C_6$alkylcarbonyl, aryl$C_1$–$C_6$alkylcarbonyl$C_1$–$C_6$alkyl, $C_1$–$C_6$alkyl-carboxy, $C_1$–$C_6$alkyl-carboxy$C_1$–$C_6$-alkyl, arylcarboxy, aryl$C_1$–$C_6$alkyl-carboxy, aryl$C_1$–$C_6$alkylcarboxy$C_1$–$C_6$alkyl, $C_1$–$C_6$alkylcarbonylamino, $C_1$–$C_6$alkylcarbonyl-amino$C_1$–$C_6$alkyl, -carbonyl$NR_7C_1$–$C_6$alkyl$COR_{11}$, aryl$C_1$–$C_6$alkyl-carbonylamino, aryl$C_1$–$C_6$alkylcarbonylamino$C_1$–$C_6$alkyl, $CONR_7R_8$, or $C_1$–$C_6$alkyl$CONR_7R_8$ wherein the alkyl and aryl groups are optionally substituted and $R_{11}$ is $NR_7R_8$, or $C_1$–$C_6$alkyl$NR_7R_8$; or $R_3$ is

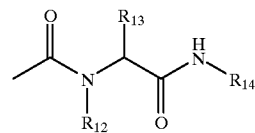

wherein $R_{12}$, $R_{13}$, and $R_{14}$ are independently hydrogen, $C_1$–$C_6$alkyl, aryl, aryl$C_1$–$C_6$alkyl and the alkyl and aryl groups are optionally substituted;

$R_4$ is hydrogen, hydroxy, $C_1$–$C_6$alkyl, aryl, aryl$C_1$–$C_6$alkyl, $NR_7R_8$, $C_1$–$C_6$alkyloxy; wherein the alkyl and aryl groups are optionally substituted;

$R_5$ is hydroxy, $C_1$–$C_6$alkyl, aryl, aryl$C_1$–$C_6$alkyl, $CF_3$, $NR_7R_8$; wherein the alkyl and aryl groups are optionally substituted;

$R_6$ is hydrogen, $C_1$–$C_6$alkyl, aryl, aryl$C_1$–$C_6$alkyl; wherein the alkyl and aryl groups are optionally substituted;

$R_7$ and $R_8$ are independently selected from hydrogen, $C_1$–$C_6$alkyl, aryl, aryl$C_1$–$C_6$alkyl, $C_1$–$C_6$alkylcarbonyl, arylcarbonyl, aryl$C_1$–$C_6$alkylcarbonyl, $C_1$–$C_6$alkyl-carboxy or aryl$C_1$–$C_6$alkylcarboxy wherein the alkyl and aryl groups are optionally substituted; or $R_7$ and $R_8$ are taken together with the nitrogen to which they are attached forming a cyclic or bicyclic system containing 3 to 11 carbon atoms and 0 to 2 additional heteroatoms selected from nitrogen, oxygen or sulfur, the ring system can optionally be substituted with at least one $C_1$–$C_6$alkyl, aryl, aryl$C_1$–$C_6$alkyl, hydroxy, $C_1$–$C_6$alkyloxy, aryl$C_1$–$C_6$alkyloxy, $C_1$–$C_6$alkyloxy$C_1$–$C_6$alkyl, $NR_9R_{10}$ or $C_1$–$C_6$alkylamino-$C_1$–$C_6$alkyl, wherein $R_9$ and $R_{10}$ are independently selected from hydrogen, $C_1$–$C_6$alkyl, aryl, aryl$C_1$–$C_6$alkyl, $C_1$–$C_6$alkylcarbonyl, arylcarbonyl, aryl$C_1$–$C_6$alkylcarbonyl, $C_1$–$C_6$alkyl-carboxy or aryl$C_1$–$C_6$alkylcarboxy; wherein the alkyl and aryl groups are optionally substituted; or $R_7$ and $R_8$ are independently a saturated or partially saturated cyclic 5, 6 or 7 membered amine or lactam;

or a salt thereof with a pharmaceutically acceptable acid or base, or any optical isomer or mixture of optical isomers, including a racemic mixture, or any tautomeric forms.

Further, preferred compounds of the invention are compounds of formula 1a or formula 1c wherein $R_{16}$ and $R_{17}$ are hydrogen.

The invention will in its broadest aspect cover the following compounds: of Formula 1b:

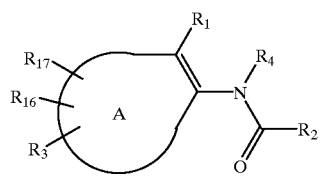

Formula 1b wherein

A is together with the double bond in Formula 1b is aryl;

$R_1$ is $COR_5$, $OR_6$, $CF_3$, nitro, cyano, $SO_3H$, $SO_2NR_7R_8$, $PO(OH)_2$, $CH_2PO(OH)_2$, $CHFPO(OH)_2$, $CF_2PO(OH)_2$, $C(=NH)NH_2$, $NR_7R_8$; or selected from the following 5-membered heterocycles:

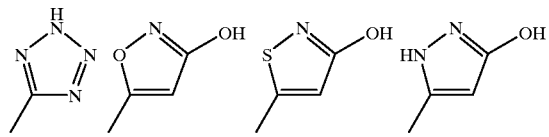

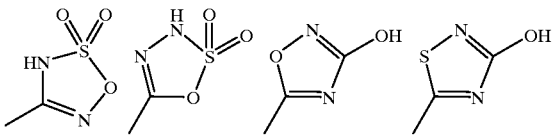

-continued

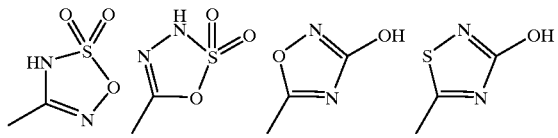

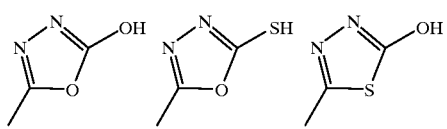

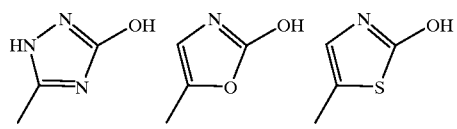

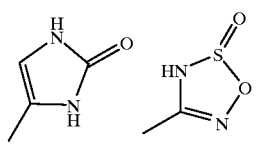

or $R_1$ is

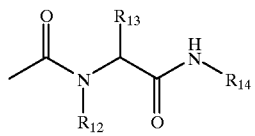

wherein $R_{12}$, $R_{13}$, and $R_{14}$ are independently hydrogen, $C_1$–$C_6$alkyl, aryl, aryl$C_1$–$C_6$alkyl and the alkyl and aryl groups are optionally substituted;

$R_2$ is $COR_5$, $OR_6$, $CF_3$, nitro, cyano, $SO_3H$, $SO_2NR_7R_8$, $PO(OH)_2$, $CH_2PO(OH)_2$, $CHFPO(OH)_2$, $CF_2PO(OH)_2$, $C(=NH)NH_2$, $NR_7R_8$; or selected from the following 5-membered heterocycles:

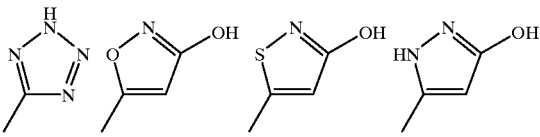

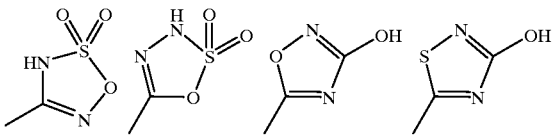

-continued

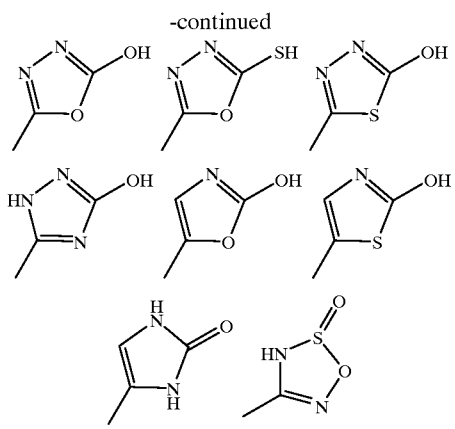

$R_3$, $R_{16}$ and $R_{17}$ are independently hydrogen, halo, nitro, cyano, trihalomethyl, $C_1-C_6$alkyl, aryl, aryl$C_1-C_6$-alkyl, hydroxy, carboxy, carboxy$C_1-C_6$alkyl, $C_1-C_6$alkyloxycarbonyl, aryloxycarbonyl, aryl$C_1-C_6$alkyloxycarbonyl, $C_1-C_6$alkyloxy, $C_1-C_6$alkyloxy$C_1-C_6$alkyl, aryloxy, aryl$C_1-C_6$alkyloxy, aryl$C_1-C_6$alkyloxy$C_1-C_6$alkyl, thio, $C_1-C_6$alkylthio, $C_1-C_6$alkylthio$C_1-C_6$alkyl, arylthio, aryl$C_1-C_6$alkylthio, aryl$C_1-C_6$alkylthio$C_1-C_6$alkyl, $NR_7R_8$, $C_1-C_6$alkylamino$C_1-C_6$alkyl, aryl$C_1-C_6$alkylamino$C_1-C_6$alkyl, di(aryl$C_1-C_6$alkyl)amino$C_1-C_6$alkyl, $C_1-C_6$alkylcarbonyl, $C_1-C_6$alkylcarbonyl$C_1-C_6$alkyl, aryl$C_1-C_6$alkylcarbonyl, aryl$C_1-C_6$alkylcarbonyl$C_1-C_6$alkyl, $C_1-C_6$alkylcarboxy, $C_1-C_6$alkylcarboxy$C_1-C_6$alkyl, arylcarboxy, arylcarboxy$C_1-C_6$alkyl, aryl$C_1-C_6$alkylcarboxy, aryl$C_1-C_6$alkylcarboxy$C_1-C_6$alkyl, $C_1-C_6$alkylcarbonylamino, $C_1-C_6$alkylcarbonylamino$C_1-C_6$alkyl, -carbonyl$NR_7C_1-C_6$alkyl$COR_{11}$, aryl$C_1-C_6$alkylcarbonylamino, aryl$C_1-C_6$alkylcarbonylamino$C_1-C_6$alkyl, $CONR_7R_8$, or $C_1-C_6$alkyl$CONR_7R_8$ wherein the alkyl and aryl groups are optionally substituted and $R_{11}$ is $NR_7R_8$, or $C_1-C_6$alkyl$NR_7R_8$; or $R_3$ is

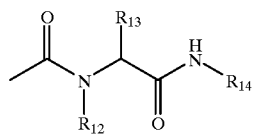

wherein $R_{12}$, $R_{13}$, and $R_{14}$ are independently hydrogen, $C_1-C_6$alkyl, aryl, aryl$C_1-C_6$alkyl and the alkyl and aryl groups are optionally substituted;

$R_4$ is hydrogen, hydroxy, $C_1-C_6$alkyl, aryl, aryl$C_1-C_6$alkyl, $NR_7R_8$, $C_1-C_6$alkyloxy; wherein the alkyl and aryl groups are optionally substituted;

$R_5$ is hydroxy, $C_1-C_6$alkyl, aryl, aryl$C_1-C_6$alkyl, $CF_3$, $NR_7R_8$; wherein the alkyl and aryl groups are optionally substituted;

$R_6$ is hydrogen, $C_1-C_6$alkyl, aryl, aryl$C_1-C_6$alkyl; wherein the alkyl and aryl groups are optionally substituted;

$R_7$ and $R_8$ are taken together with the nitrogen to which they are attached forming a saturated, partially saturated or aromatic cyclic, bicyclic or tricyclic ring system containing 3 to 14 carbon atoms and 0 to 3 additional heteroatoms selected from nitrogen, oxygen or sulfur, the ring system can optionally be substituted with at least one $C_1-C_6$alkyl, aryl, aryl$C_1-C_6$alkyl, hydroxy, oxo, $C_1-C_6$alkyloxy, aryl$C_1-C_6$alkyloxy, $C_1-C_6$alkyloxy$C_1-C_6$alkyl, $NR_9R_{10}$ or $C_1-C_6$alkylamino$C_1-C_6$alkyl, wherein $R_9$ and $R_{10}$ are independently selected from hydrogen, $C_1-C_6$alkyl, aryl, aryl$C_1-C_6$alkyl, $C_1-C_6$alkylcarbonyl, arylcarbonyl, aryl$C_1-C_6$alkylcarbonyl, $C_1-C_6$alkylcarboxy or aryl$C_1-C_6$alkylcarboxy; wherein the alkyl and aryl groups are optionally substituted; or $R_7$ and $R_8$ are independently a saturated or partially saturated cyclic 5, 6 or 7 membered amine, imide or lactam;

or a salt thereof with a pharmaceutically acceptable acid or base, or any optical isomer or mixture of optical isomers, including a racemic mixture, or any tautomeric forms.

The following compounds are preferred:
2-(Oxalyl-amino)benzoic acid;
2-Methyl-6-(oxalyl-amino)benzoic acid;
2-(Oxalyl-amino)-5-iodo-benzoic acid;
2-(Aminooxalyl-amino)benzoic acid;
2-(Oxalyl-amino)-4-fluoro-benzoic acid;
2-(Oxalyl-amino)-4-(3-hydroxy-pyridin-2-ylsulfanyl)benzoic acid;
2-(Oxalyl-amino)-4-(1-imidazol-2-ylsulfanyl)benzoic acid;
2-(Oxalyl-amino)-4-(benzooxazol-2-ylsulfanyl)benzoic acid;
2-(Oxalyl-amino)-4-(4-phenyl-thiazol-2-ylsulfanyl) acid;
2-(Oxalyl-amino)-4-(3-ethoxycarbonylphenoxy)benzoic acid;
2-(Oxalyl-amino)-4-benzylamino-benzoic acid;
2-(Oxalyl-amino)-4-(cyclopropylmethyl-amino)benzoic acid;
2-(Oxalyl-amino)-4-(3-methyl-butylamino)benzoic acid;
2-(Hydrazinooxalyl-amino)benzoic acid;
3-(Oxalyl-amino)naphthalene-2-carboxylic acid;
2-((5-Thioxo-4,5-dihydro[1,3,4]oxadiazole-2-carbonyl)amino)benzoic acid;
N-(2-(3,5-Dichloro-phenoxy)phenyl)oxalamic acid;
2-(Oxalyl-amino)-3-hydroxy-benzoic acid;
2-(Oxalyl-amino)-5-hydroxy-benzoic acid;
2-(Oxalyl-amino)-4-nitro-benzoic acid;
2-(Oxalyl-amino)-3,5-diiodo-benzoic acid;
2-(Oxalyl-amino)-3,5-dimethyl-benzoic acid;
2-(Oxalyl-amino)-5-methyl-benzoic acid;
2-(Oxalyl-amino)-4,5-dimethoxy-benzoic acid;
3-(Oxalyl-amino)-phthalic acid;
2-(Oxalyl-amino)-4-(2-hydroxy-cyclohexylamino)benzoic acid;
2-(Oxalyl-amino)-4-((2-hydroxy-ethylsmethyl-amino) benzoic acid;
2-(Oxalyl-amino)-4-(2,2,6,6-tetramethyl-piperidin-4-ylamino)benzoic acid;
2-(2-Hydroxy-cyclohexylamino)-6-(oxalyl-amino)benzoic acid;
2-[(2-Hydroxy-ethyl)-methyl-amino]-6-(oxalyl-amino) benzoic acid;
2-(Oxalyl-amino)-6-(2,2,6,6-tetramethyl-piperidin-4-ylamino)benzoic acid;
2-(Oxalyl-amino)-4-(pyridin-3-ylamino)benzoic acid;
2-(Oxalyl-amino)-4-(3-hydroxy-piperidin-1-yl)benzoic acid;

2-(Oxalyl-amino)-4-(1-methyl-1H-imidazol-2-ylsulfanyl) benzoic acid;
2-(Oxalyl-amino)-6-(pyridin-3-ylamino)benzoic acid;
2-(3-Hydroxy-piperidin-1-yl)-6-(oxalyl-amino)benzoic acid;
2-(1-Methyl-1H-imidazol-2-ylsulfanyl)-6-(oxalyl-amino) benzoic acid;
2-(Oxalyl-amino)-4-(2-morpholin-4-yl-ethylamino)benzoic acid;
2-(Oxalyl-amino)-4-(benzenesulfonyl-(2-morpholin-4-yl-ethyl)-amino)benzoic acid;
2-(Oxalyl-amino)-4-[acetyl-(2-morpholin-4-yl-ethyl) amino]benzoic acid;
2-(2-Morpholin-4-yl-ethylamino)-6-(oxalyl-amino)benzoic acid;
2-(Acetyl-(2-morpholin-4-yl-ethyl-amino)-6-(oxalyl-amino) benzoic acid;
2-(Oxalyl-amino)-4-cyclopentylamino-benzoic acid;
2-(Oxalyl-amino)-4-(benzenesulfonyl-clopentyl-amino) benzoic acid;
2-(Oxalyl-amino)-4-(acetyl-cyclopentyl-amino)benzoic acid;
2-Cyclopentylamino-6-(oxalyl-amino)benzoic acid;
2-(Benzenesulfonyl-cyclopentyl-amino)-6-(oxalyl-amino) benzoic acid;
2-(Acetyl-cyclopentyl-amino-6-(oxalyl-amino)benzoic acid;
4-(Oxalyl-amino)biphenyl-3-carboxylic acid;
3-(Oxalyl-amino)-isonicotinic acid;
5-(Oxalyl-amino)-2,6-dioxo-1,2,3,6-tetrahydro-pyrimidine-4-carboxylic acid;
2-(Oxalyl-amino)nicotinic acid;
6-Chloro-5-isopropylamino-3-(oxalyl-amino)pyrazine-2-carboxylic acid;
5,6-Dichloro-3-(oxalyl-amino)-pyrazine-2-carboxylic acid;
3-(Oxalyl-amino)-pyridazine-4-carboxylic acid;
4-(Oxalyl-amino)-pyrimidine-5-carboxylic acid; and
3-(Oxalyl-amino)-pyrazine-2-carboxylic acid.

PHARMACOLOGICAL METHODS

The compounds are evaluated for biological activity with a truncated form of PTP1B (corresponding to the first 321 amino acids), which was expressed in *E. coli* and purified to apparent homogeneity using published procedures well known to those skilled in the art. The enzyme reactions are carried out using standard conditions essentially as described by Burke et al. (*Biochemistry* 35; 15989–15996 (1996)). The assay conditions are as follows. Appropriate concentrations of the compounds of the invention are added to the reaction mixtures containing different concentrations of the substrate, p-nitrophenyl phosphate (range: 0.16 to 10 mM—final assay concentration). The buffer used was 100 mM sodium acetate pH 5.5, 50 mM sodium chloride, 0.1% (w/v) bovine serum albumin and 5 mM dithiothreitol (total volume 100 ml). The reaction was started by addition of the enzyme and carried out in microtiter plates at 25° C. for 60 minutes. The reactions are stopped by addition of NaOH. The enzyme activity was determined by measurement of the absorbance at 405 nm with appropriate corrections for absorbance at 405 nm of the compounds and p-nitrophenyl phosphate. The data are analyzed using nonlinear regression fit to classical Michaelis Menten enzyme kinetc models. Inhibition is expressed as $K_i$ values in $\mu M$. The results of representative experiments are shown in Table 1.

TABLE 1

Inhibition of classical PTP1B by compounds of the invention

| Example no. | PTP1B $K_i$ values ($\mu M$) |
|---|---|
| 1 | 20 |
| 2 | 9.9 |

Further, the compounds are evaluated for biological activity as regards their effect as inhibitors of PTPα in essentially the same way as described for inhibition of PTP1B. Derived from their activity as evaluated above the compounds of the invention may be useful in the treatment of diseases selected from the group consisting of type I diabetes, type II diabetes, impaired glucose tolerance, insulin resistance and obesity. Furthermore, derived from their activity as evaluated above, the compounds of the invention may be useful in the treatment of diseases selected from the group consisting of immune dysfunctions including autoimmunity, diseases with dysfunctions of the coagulation system, allergic diseases including asthma, osteoporosis, proliferative disorders including cancer and psoriasis, diseases with decreased or increased synthesis or effects of growth hormone, diseases with decreased or increased synthesis of hormones or cytokines that regulate the release of/or response to growth hormone, diseases of the brain including Alzheimer's disease and schizophrenia, and infectious diseases.

THE SYNTHESIS OF THE COMPOUNDS

In accordance with one aspect of the invention, the compounds of the invention are prepared as illustrated in the following reaction scheme:

Method A

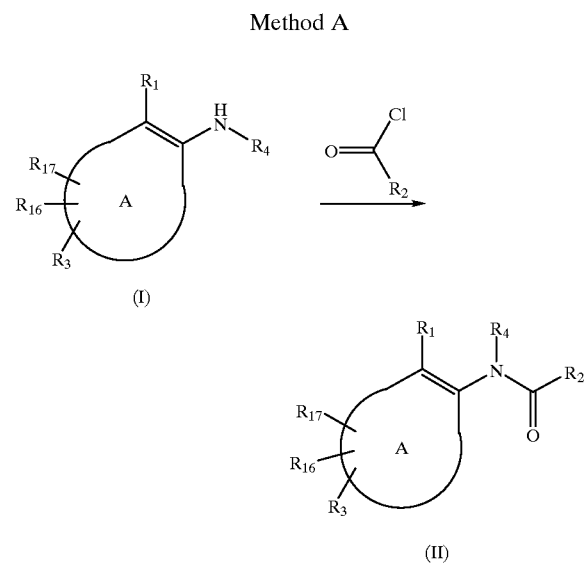

By allowing an amino substituted compound of formula (I) to react with an activated carboxylic acid (e.g. an acid chloride) of formula (II), wherein A, $R_1$, $R_2$, $R_3$, $R_4$, $R_{16}$ and $R_{17}$ are defined as above.

Method B

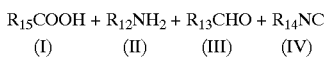

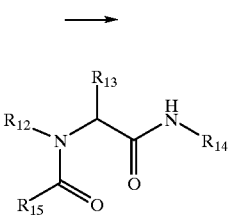

By allowing a carboxylic acid (I), a primary amine (II) and an aldehyde (III) to react with a isocyanide (IV) wherein $R_{12}$, $R_{13}$, $R_{14}$, and $R_{15}$ are independently selected from the group consisting of hydrogen, $C_1$–$C_6$alkyl, aryl, aryl$C_1$–$C_6$alkyl as defined above and the alkyl and aryl groups are optionally substituted as defined above; or $R_{12}$, $R_{13}$, $R_{14}$, and $R_{15}$ are independently selected from

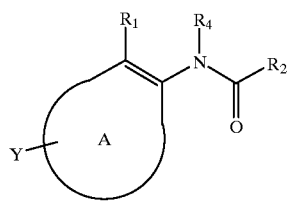

wherein Y indicates attachment point for $R_{12}$, $R_{13}$, $R_{14}$, and $R_{15}$, and A, $R_1$ $R_2$ and $R_4$ are defined as above.

In a preferred method, the above described four component Ugi reaction can be carried out by attaching any one of the components to a solid support. Hence, the synthesis can be accomplished in a combinatorial chemistry fashion.

General procedure for the Preparation of Acetoxymethyl Esters (C. Schultz et al., The Journal of Biological Chemistry, 1993, 268, 6316–6322.): A carboxylic acid (1 equivalent) was suspended in dry acetonitrile (2 ml per 0.1 mmol). Diisopropyl amine (3.0 equivalents) was added followed by bromomethyl acetate (1.5 equivalents). The mixture was stirred under nitrogen overnight at room temperature. Acetonitrile was removed under reduced pressure to yield an oil which was diluted in ethylacetate and washed water (3×). The organic layer was dried over anhydrous magnesium sulfate. Filtration followed by solvent removal under reduced pressure afforded a crude oil. The product was purified by column chromatography on silica gel, using an appropriate solvent system.

The present invention also has the objective of providing suitable topical, oral, and parenteral pharmaceutical formulations for use in the novel methods of treatment of the present invention. The compounds of the present invention may be administered orally as tablets, aqueous or oily suspensions, lozenges, troches, powders, granules, emulsions, capsules, syrups or elixirs. The composition for oral use may contain one or more agents selected from the group of sweetening agents, flavoring agents, coloring agents and preserving agents in order to produce pharmaceutically elegant and palatable preparations. The tablets contain the acting ingredient in admixture with non-toxic pharmaceutically acceptable excipients which are suitable for the manufacture of tablets. These excipients may be, for example, (1) inert diluents, such as calcium carbonate, lactose, calcium phosphate or sodium phosphate; (2) granulating and disintegrating agents, such as corn starch or alginic acid; (3) binding agents, such as starch, gelatin or acacia; and (4) lubricating agents, such as magnesium stearate, stearic acid or talc. These tablets may be uncoated or coated by known techniques to delay disintegration and absorption in the gastrointestinal tract and thereby provide a sustained action over a longer period. For example, a time delay material such as glyceryl monostearate or glyceryl distearate may be employed. Coating may also be performed using techniques described in the U.S. Pat. Nos. 4,256,108; 4,160,452; and 4,265,874 to form osmotic therapeutic tablets for control release.

Formulations for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, such as peanut oil, liquid paraffin or olive oil.

Aqueous suspensions normally contain the active materials in admixture with excipients suitable for the manufacture of aqueous suspension. Such expicients may be (1) suspending agent such as sodium carboxymethyl cellulose, methyl cellulose, hydroxypropylmethyl-cellulose, sodium alginate, polyvinylpyrrolidone, gum tragacanth and gum acacia; (2) dispersing or wetting agents which may be (a) naturally occurring phosphatide such as lecithin; (b) a condensation product of an alkylene oxide with a fatty acid, for example, polyoxyethylene stearate; (c) a condensation product of ethylene oxide with a long chain aliphatic alcohol, for example, heptadecaethylen-oxycetanol; (d) a condensation product of ethylene oxide with a partial ester derived from a fatty acid and hexitol such as polyoxyethylene sorbitol monooleate, or (e) a condensation product of ethylene oxide with a partial ester derived from fatty acids and hexitol anhydrides, for example, polyoxyethylene sorbitan monooleate.

The pharmaceutical compositions may be in the form of a sterile injectable aqueous or oleagenous suspension. This suspension may be formulated according to known methods using those suitable dispersing or wetting agents and suspending agents which have been mentioned above. The sterile injectable preparation may also a sterile injectable solution or suspension in a non-toxic parenterally-acceptable diluent or solvent, for example, as a solution in 1,3-butanediol. Among the acceptable vehides and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

The compounds of the invention may also be administered in the form of suppositories for rectal administration. These compositions can be prepared by mixing the drug with a suitable non-irritating excipient which is solid at ordinary temperature but liquid at the rectal temperature and will therefore melt in the rectum to release the drug. Such materials are cocoa butter and polyethylene glycols. The compounds of the present invention may also be administered in the form of liposome delivery systems, such as small unilamellar vesicles, large unilamellar vesicles, and multi-lamellar vesicles. Liposomes can be formed from a variety of phospholipids, such as cholesterol, stearylamine, or phosphatidyl-cholines. For topical use, creams, ointments, jellies, solutions or suspensions, etc., containing the compounds of Formula 1 are employed.

Dosage levels of the compounds of the present invention are of the order of about 0.5 mg to about 100 mg per kilogram body weight, with a preferred dosage range between about 20 mg to about 50 mg per kilogram body weight per day (from about 25 mg to about 5 g's per patient per day). The amount of active ingredient that may be combined with the carrier materials to produce a single dosage will vary depending upon the host treated and the particular mode of administration. For example, a formulation intended for oral administration to humans may contain 5 mg to 1 g of an active compound with an appropriate and convenient amount of carrier material which may vary from about 5 to about 95 percent of the total composition. Dosage unit forms will generally contain between from about 5 mg to about 500 mg of active ingredient.

It will be understood, however, that the specific dose level for any particular patient will depend upon a variety of factors including the activity of the specific compound employed, the age, body weight, general health, gender, diet, time of administration, route of administration, rate of excretion, drug combination and the severity of the particular disease undergoing therapy. The dosage needs to be individualized by the clinician.

EXAMPLES

The process for preparing compounds of Formula 1 and preparations containing them is further illustrated in the following examples, which, however, are not to be construed as limiting.

Hereinafter, TLC is thin layer chromatography, $CDCl_3$ is deuterio chloroform, $CD_3OD$ is tetradeutereio methanol and DMSO-$d_6$ is hexadeuterio dimethylsulfoxide. The structures of the compounds are confirmed by either elemental analysis or NMR, where peaks assigned to characteristic protons in the title compounds are presented where appropriate. $^1H$ NMR shifts ($\delta_H$) are given in parts per million (ppm) downfield from tetramethylsilane as internal reference standard. M.p.: is melting point and is given in ° C. and is not corrected. Column chromatography was carried out using the technique described by W. C. Still et al., *J. Org. Chem.* 43: 2923 (1978) on Merck silica gel 60 (Art. 9385). HPLC analyses are performed using 5 µm C18 4×250 mm column eluted with various mixtures of water and acetonitrile, flow=1 ml/min, as described in the experimental section.

Compounds used as starting material are either known compounds or compounds which can readily be prepared by methods known per se.

Example 1

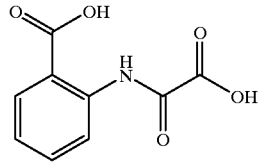

2-(Oxalyl-amino)benzoic acid;

To a stirred solution of anthranilic acid (20.1 g, 0.15 mol) in dry tetrahydrofuran (250 ml) was added dropwise ethyl oxalyl chloride (10.0 g, 0.073 mol). The resulting reaction mixture was stirred at room temperature for 15 min. filtered and the solvent evaporated in vacuo affording crude 16.4 g (94%) of 2-(ethoxyoxalyl-amino)benzoic acid as an oil.

To a solution of the above benzoic acid (10.0 g, 42 mmol) in ethanol (350 ml) was added a solution of sodium hydroxide (3.7 g, 92 mmol) in water (100 ml). The resulting reaction mixture was stirred at room temperature for 60 h. Concentrated hydrochloric acid was added to pH=1 and the precipitate was filtered off and washed with water (3×100 ml), diethyl ether (3×80 ml) and dried in vacuo affording 7.1 g (81%) of the title compound as a solid.

M.p.: 214–215° C.:

Calculated for $C_9H_7NO_5$, 0.2 $H_2O$; C, 51.68%; H, 3.37%; N, 6.70%. Found: C, 50.96%; H, 3.32%; N, 6.52%.

By a similar procedure as described in Example 1 the following compounds have been prepared.

Example 2

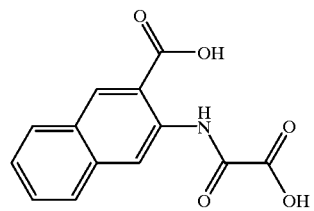

3-(Oxalyl-amino)naphthalene-2-carboxylic acid;

M.p.: 227–228° C.: Calculated for $C_{13}H_9NO_5$; C, 60.24%; H, 3.50%; N, 5.40%. Found: C, 59.98%; H,3.46%; N, 5.25%.

Example 3

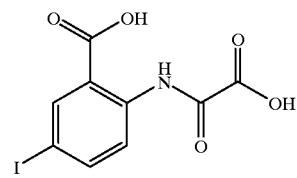

2-(Oxalyl-amino)-5-iodo-benzoic acid;

MS(ES): m/z=326 (M+1); Calculated for $C_9H_6NIO_5$, 0.75×$H_2O$; C, 31.01%; H, 2.17%; N, 4.02%. Found: C, 31.14%; H, 2.33%; N, 3.76%.

Example 4

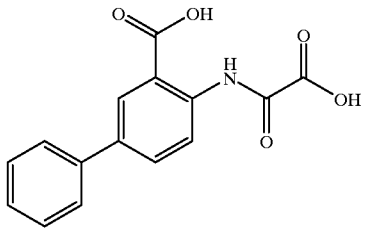

4-(Oxalyl-amino)-biphenyl-3-carboxylic acid;

To a suspension of 5-bromo-2-amino-benzoic acid methyl ester (3.0 g, 13,04 mmol), tetrakis(triphenylphosphine)palladium(0) (0.5 g, 0.44 mmol), toluene (40 ml) and 2 N aqueous sodium carbonate (14.8 ml) was added a solution of phenylboronic acid (2.2 g, 17.73 mmol) in methanol (10 ml) at room temperature. The resulting reaction mixture was heated at reflux temperature for 4 h. cooled and diluted with water (50 ml). The insoluble matter was filtered off and the phases were separated. The aqueous phase was extracted with ethyl acetate (100 ml) and the combined organic phases were washed with water (2×80 ml), diluted aqueous ammoniac (80 ml) and saturated aqueous sodium chloride (80 ml). The organic phase was dried ($MgSO_4$), filtered and evaporated in vacuo affording 3.4 g of crude 4-amino-biphenyl-3-carboxylic acid methyl ester which was purified on silicagel (1 l) using a mixture of ethyl acetate and heptane (1:3) as eluent. Pure fractions were collected and evaporated in vacuo affording 2.7 g (91%) of 4-amino-biphenyl-3-carboxylic acid methyl ester.

4-Aminobiphenyl-3-carboxylic acid methyl ester was converted into the title compound by a similar procedure as described in Example 1.

M.p.: 223–224° C.; Calculated for $C_{15}H_{11}NO_5, 0.5 \times H_2O$; C, 61.23%; H, 4.11%; N, 4.76%. Found: C, 60.96%; H, 4.01%; N, 4.62%.

Example 5

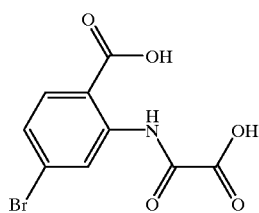

4-Bromo-2-(oxalyl-amino)-benzoic acid;

$^1$H NMR (400 MHz, $CD_3OD$) δ 8.71 (d, J=7.5 Hz, 1H), 8.25 (s, 1H), 7.80 (d, J=7.5 Hz, 1H). MS: ESI (−): 288 [M−1($^{81}$Br)], 287 (M−1($^{80}$Br)].

Example 6

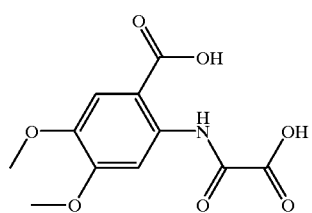

4,5-Dimethoxy-2-(oxalyl-amino)-benzoic acid;

$^1$H NMR (400 MHz, $CD_3OD$) δ 8.42 (s, 1H), 7.60 (s, 1H), 3.95 (s, 3H), 3.86 (s, 3H). MS: ESI (−): 268 [M−1].

Example 7

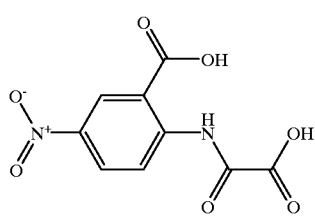

5-Nitro-2-(oxalyl-amino)-benzoic acid;

$^1$H NMR (400 MHz, $CD_3OD$) δ 8.90 (d, J=7.5 Hz, 2H), 8.42 (s, 1H). MS: ESI (−): 253 [M−1].

Example 8

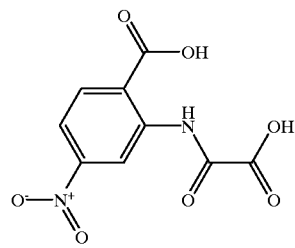

4-Nitro-2-(oxalyl-amino)-benzoic acid;

$^1$H NMR (400 MHz, $CD_3OD$) δ 9.60 (s, 1H), 8.36 (m, 1H), 8.02 (m, 1H). MS: ESI (−): 253 [M−1].

Example 9

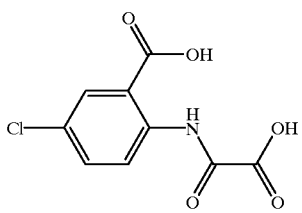

5-Chloro-2-(oxalyl-amino)-benzoic acid;

$^1$H NMR (400 MHz, $CD_3OD$) δ 8.72 (d, J=7.5 Hz, 1H), 8.10 (s, 1H), 7.60 (d, J=7.5 Hz, 1H). MS: ESI (−): 242 [M−1($^{35}$Cl)], 244 [M−1($^{37}$Cl)].

Example 10

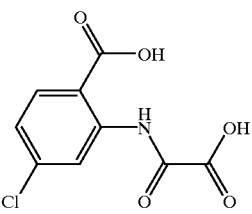

4-Chloro-2-(oxalyl-amino)-benzoic acid;

$^1$H NMR (400 MHz, $CD_3OD$) δ 8.80 (s, 1H), 8.10 (d, J=7.5 Hz, 1H), 7.22 (d, J=7.5 Hz, 1H). MS: ESI (−): 242 [M−1($^{35}$Cl)], 244 [M−1($^{37}$Cl)].

Example 11

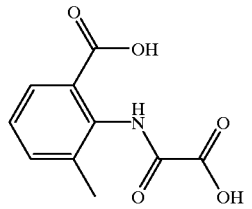

3-Methyl-2-(oxalyl-amino)-benzoic acid;

$^1$H NMR(400 MHz, DMSO-$d_6$) δ 2.2 (s, 3H), 7.2–7.7 (m, 3H), 10.5 (s, 1H), 12.9 (s, 1H).

Example 12

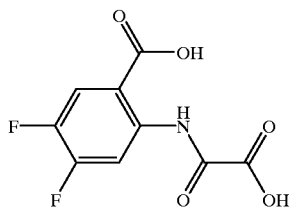

4,5-Difluoro-2-(oxalyl-amino)-benzoic acid;

$^1$H NMR (300 MHz, DMSO-d$_6$) δ 8.03 (m, 1H), 8.61 (dd, 1H), 12.55 (s, 1H, NHCO).

Example 13

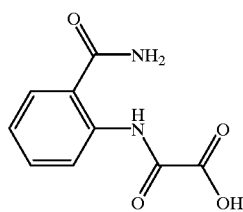

N-(2-Carbamoyl-phenyl)-oxalamic acid;

$^1$H NMR (300 MHz, DMSO-d$_6$) δ 7.20 (t, 1H), 7.55 (t, 1H), 7.73 (bs, 1H, CONH$_2$), 7.83 (d, 1H), 8.30 (bs, 1H, CONH$_2$), 8.52 (d, 1H), 12.9 (s, 1H, NHCO).

Example 14

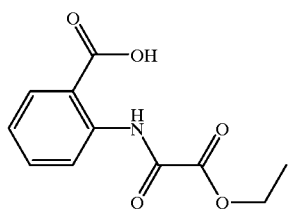

2-(Ethoxyoxalyl-amino)-benzoic acid;

$^1$H NMR (300 MHz, DMSO-d$_6$) δ 1.33 (t, 3H), 4.30 (q, 2H), 7.24 (t, 1H), 7.65 (t, 1H), 8.03 (d, 1H), 8.56 (d, 1H), 12.6 (s, 1H, NHCO).

Example 15

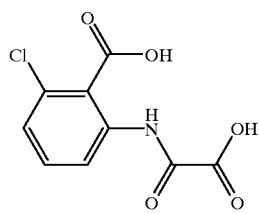

6-Chloro-2-(oxalyl-amino)-benzoic acid;

$^1$H NMR (400 MHz, DMSO-d$_6$) δ 10.68 (bs, 1H), 8.06 (d, J=9 Hz, 1H), 7.43 (t, J=9 Hz, 1H), 7.27 (d, J=9 Hz, 1H).

Example 16

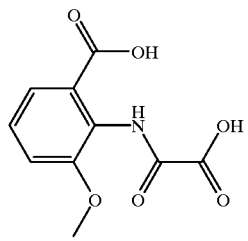

3-Methoxy-2-(oxalyl-amino)-benzoic acid;

$^1$H NMR (400 MHz, DMSO-d$_6$) δ 9.98 (bs, 1H), 7.37–7.25 (m, 3H), 3.80 (s, 3H).

Example 17

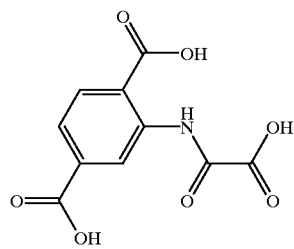

2-(Oxalyl-amino)-terephthalic acid;

$^1$H NMR (400 MHz, DMSO-d$_6$) ε 7.28 (s, 1H), 8.22 (d, J=9 Hz, 1H), 7.75 (d, J=9 Hz, 1H).

Example 18

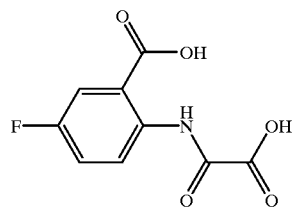

5-Fluoro-2-(oxalyl-amino)-benzoic acid;

$^1$H NMR (400 MHz, CD$_3$OD) δ 7.50 (m, 1H), 7.25 (m, 1H), 7.22 (m, 1H). MS m/z 227.2 (M−1).

Example 19

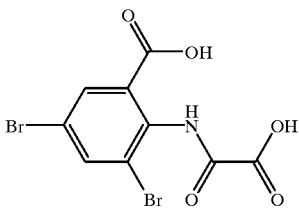

3,5-Dibromo-2-(oxalyl-amino)-benzoic acid;

$^1$H NMR (400 MHz, CD$_3$OD) δ 8.08 (s, 1H), 8.05 (s, 1H). MS m/z 366.1 (M−1).

Example 20

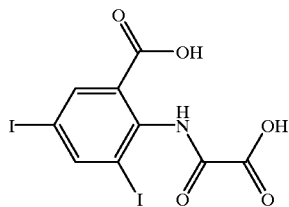

3,5-Diiodo-2-(oxalyl-amino)-benzoic acid;
$^1$H NMR (400 MHz, CD$_3$OD) δ 8.45 (s, 1H), 8.25 (s, 1H). MS m/z 460.1 (M−1).

Example 21

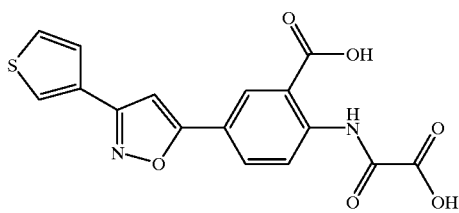

2-(Oxalyl-amino)-5-(3-thiophen-3-yl-isoxazol-5-yl)-benzoic acid;

To a solution of thiophene-3-carboxaldehyde (2.0 g, 18 mmol) in 1,4-dioxane (6.0 ml) was added hydroxylamine hydrochloride (1.24 g, 18 mmol) and triethylamine (2.5 ml, 18 mmol). The mixture was sonicated for 0.5 h and stirred at room temperature for 116 h and at 35° C. for 48 hour. The solvent was removed in vacuo and the residue was dissolved in dichloromethane and washed with water, dried (MgSO$_4$), filtered and evaporated in vacuo affording 1.97 g (87%) of thiophene-3-carbaldehyde oxime as an oil.

To a solution of the above thiophene-3-carbaldehyde oxime (120 mg, 0.99 mmol) and 2-(tert-butoxyoxalyl-amino)-5-ethynyl-benzoic acid methyl ester (100 mg, 0.33 mmol) in tetrahydrofuran (2.5 ml) stirred at room temperature was added 0.75 M bleach (1.3 ml, 0.99 mmol). The solution was first stirred at room temperature for 24 h and then at 35° C. for 24 h. The solvent was evaporated in vacuo and the residue was dissolved in dichloromethane, washed with water, brine and dried (MgSO$_4$), filtered and evaporated in vacuo. The residual film was purified by preparative TLC affording 21 mg, (15%) of 2-(tert-butoxyoxalyl-amino-5-(3-thiophen-3-yl-isoxazol-5-yl)-benzoic acid methyl ester as an oil.

$^1$H NMR (400 MHz, CDCl$_3$) δ 12.75 (s, 1H), 8.92 (d, 1H, J=11 Hz), 8.59 (s, 1H), 8.06 (d, 1H, J=11 Hz), 7.91 (s, 1H), 7.59 (d, 1H, J=7 Hz), 7.28 (d, 1H, J=7 Hz), 6.90 (s, 1H), 4.07 (s 3H), 1.65 (s, 9H).

The above 2-(tert-butoxyoxalyl-amino)-5-(3-thiophen-3-yl-isoxazol-5-yl)-benzoic acid methyl ester (10 mg, 0.023 mmol) was dissolved in 20% trifluoroacetic acid/dichloromethane (0.3 ml) and stirred at room temperature for 21 h. The solvent was removed in vacuo affording 8.4 mg (98%) of 2-(oxalyl-amino)-5-(3-thiophen-3-yl-isoxazol-5-yl)-benzoic acid methyl ester as a solid.

$^1$H NMR (400 MHz, CD$_3$OD) δ 12.75 (s, 1H), 8.95 (d, 1H, J=11 Hz), 8.62 (s, 1H), 8.18 (d, 1H, J=11 Hz), 7.75 (m, 1H), 7.65 (m, 1H), 7.60 (s, 1H), 4.07 (s, 3H).

To a solution of 2-(oxalyl-amino)-5-(3-thiophen-3-yl-isoxazol-5-yl)-benzoic acid methyl ester (8.4 mg, 0.023 mmol) in methanol (1.5 ml) and tetrahydrofuran (0.5 ml) at room temperature was added 1 M lithium hydroxide (90 μl, 0.090 mmol). The solution was stirred for 48 h. The solvent was removed in vacuo and the residue was redissolved in water. The solution was acidified with 1 N hydrochloric acid to pH=1 and extracted with ethyl acetate. The combined extracts were washed with brine, dried (MgSO$_4$), filtered and the solvent evaporated i vacuo affording 6.4 mg (79%) of the title compound as a solid.

$^1$H NMR (400 MHz, CD$_3$OD) δ 8.75 (d, 1H, J=11 Hz), 8.70 (s, 1H), 7.95 (s, 1H), 7.82 (d, 1H, J=11 Hz), 7.70 (m, 1H), 7.60 (m, 1H). MS m/z: 357(M−1).

Example 22

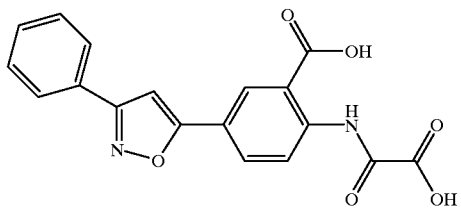

2-(Oxalyl-amino)-5-(3-phenyl-isoxazol-5-yl)-benzoic acid;

To a solution of benzaldehyde (2.0 g, 19 mmol) in 1,4-dioxane (6.0 ml) was added hydroxylamine hydrochloride (1.3 g, 19 mmol) and triethylamine (2.6 ml, 19 mmol). The mixture was sonicated for 0.5 h and stirred at room temperature for 116 h and at 35° C. for 24 h. The solvent was removed in vacuo and the residue was dissolved in dichloromethane and washed with water, dried (MgSO$_4$), filtered and evaporated in vacuo affording 1.9 g (84%) of benzaldehyde oxime as an oil.

$^1$H NMR (400 MHz, CDCl$_3$) δ 8.18 (s, 1H), 7.60 (m, 2H), 7.41 (m, 3H).

To a solution of benzaldehyde oxime (120 mg, 0.99 mmol) and 2-(tert-butoxyoxalyl-amino)-5-ethynyl-benzoic acid methyl ester (100 mg, 0.33 mmol) in tetrahydrofuran (2.5 ml) stirred at room temperature was added 0.75 M bleach (1.3 ml, 0.99 mmol). The solution was first stirred at room temperature for 24 h and then at 35° C. for 24 h. The solvent was evaporated in vacuo and the residue was dissolved in dichloromethane. The solution was washed with water, brine, dried (MgSO$_4$), filtered and the solvent evaporated in vacuo. The residue was washed with diethyl ether to get a solid precipitate which was filtered off yielding 59 mg (42%) of 2-(tert-butoxyoxalyl-amino)-5-(3-phenyl-isoxazol-5-yl)-benzoic acid methyl ester as a solid.

$^1$H NMR (400 MHz, CDCl$_3$) δ 12.75 (s, 1H), 8.85 (d, 1H, J=11 Hz), 8.62 (s, 1H), 8.06 (d, 1H, J=11 Hz), 7.91 (m, 2H), 7.52 (m, 3H), 6.90 (s, 1H), 4.07 (s 3H), 1.65 (s, 9H).

The above 2-(tert-butoxyoxalyl-amino-5-(3-phenyl-isoxazol-5-yl)-benzoic acid methyl ester (28 mg, 0.07 mmol) was dissolved in 20% trifluoroacetic acid/dichloromethane (0.5 ml) and stirred at room temperature for 6 h. The solvent was removed in vacuo affording 25 mg (100%) of 2-amino-5-(3-phenyl-isoxazol-5-yl)-benzoic acid methyl ester as a solid.

$^1$H NMR (400 MHz, CDCl$_3$) δ 12.75 (s, 1H), 8.85 (d, 1H, J=11 Hz), 8.62 (s, 1H), 8.15 (d, 1H, J=11 Hz), 7.91 (m, 2H), 7.52 (m, 3H), 6.90 (s, 1H), 4.07 (s 3H).

To a solution of the above 2-amino-5-(3-phenyl-isoxazol-5-yl)-benzoic acid methyl ester (12.5 mg, 0.034 mmol) in methanol (2.5 ml) and tetrahydrofuran (1.0 ml) at room temperature was added 1 M lithium hydroxide (1.4 ml, 0.136 mmol). The solution was stirred for 12 h and the solvent was removed in vacuo. The residue was dissolved in water acidified with 1 N hydrochloric acid to pH=1 and extracted with ethyl acetate. The organic extract was washed with brine, dried (MgSO₄), filtered and the solvent evaporated in vauco affording 7.7 mg (64%) of title compound as a solid.

$^1$H NMR (400 MHz, CD$_3$OD) δ 8.91 (d, 1H, J=11 Hz), 8.62 (s, 1H), 8.15 (d, 1H, J=11 Hz), 7.91 (m, 2H), 7.49 (m, 3H), 7.25 (s, 1H), 4.07 (s 3H). LC/MS m/z: 351(M−1).

Example 23

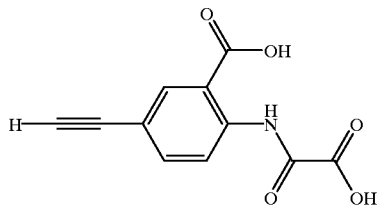

5-Ethynyl-2-(oxalyl-amino)-benzoic acid;

A solution of 2-(tert-butoxyoxalyl-amino-5-iodo-benzoic acid (5.0 g, 12.8 mmol, prepared as described in example 27) and N,N-dimethylformamide di-tertbutylacetal (12 ml, 51.2 mmol) in toluene (100 ml) was heated at reflux for 20 h. The reaction was cooled to room temperature, concentrated in vauo and the residue dissolved in ethyl acetate (150 ml). The ethyl acetate phase was washed with water (3×35 ml), brine (20 ml) and the volatles evaporated in vacuo. The residue was purified by silica gel chromatography using 25% ethyl acetate/hexane as eluent. Pure fractions were combined and concentrated in vacuo to yield 2.3 g of 2-(tert-butoxyoxalyl-amino)-5-iodo-benzoic acid tert-butyl ester as an oil.

$^1$H NMR (400 MHz, CDCl$_3$) δ 8.54 (d, J=9 Hz, 1H), 8.27 (s, 1H), 7.83 (d, J=9 Hz, 1H), 1.62 (s, 18H).

2-(tert-Butoxyoxalyl-amino)-5-iodo-benzoic acid tert-butyl ester (0.83 g, 1.86 mmol), trimethylsilyl acetylene (2 ml), and triethylamine (1 ml, 7.44 mmol) were dissolved in N,N-dimethylformamide (5 ml) and the solution purged with argon. Dichlorobis-(triphenylphosphine)palladium(II) (26 mg, 0.15 mmol) and copper(I)iodide (4 mg, 0.15 mmol) were added and the reaction stirred at 60° C. under argon for 5 h. The crude mixture was diluted with ethyl acetate (40 ml) and washed with water (3×10 ml) and brine (2×10 ml). The solvent was evaporated in vacuo to yield 0.77 g (99%) of 2-(tert-butoxyoxalyl-amino)-5-trimethylsilanylethyny-benzoic acid tert-butyl ester.

$^1$H NMR (400 MHz, CDCl$_3$) δ 12.59 (s, 1H), 8.71 (d, J=9 Hz, 1H), 8.07 (d, J=9 Hz, 1H), 1.62 (s, 9H), 1.61 (s, 9H), 0.25 (s, 9H).

2-(tert-Butoxyoxalyl-amino)-5-trimethylsilanylethyny-benzoic acid tert-butyl ester (0.57 g, 1.37 mmol) was dissolved in tetrahydrofuran (5 ml) and treated with a 0.9 M solution of tetrabutylammonium fluoride and acetic acid (2:3) in tetrahydrofuran (1.7 ml, 1.51 mmol) for 3 h. The volatiles were evaporated in vacuo and the crude material extracted into ethyl acetate (35 ml). The ethyl acetate extract was washed with 1N hydrochloric acid (5 ml), saturated sodium bicarbonate (5 ml), brine (5 ml) and evaporated in vacuo affording 0.36 g (76%) of 2-(tert-butoxyoxalyl-amino)-5-ethynyl-benzoic acid tert-butyl ester as an oil.

$^1$H NMR (400 MHz, CDCl$_3$) δ 8.74 (d, J=10 Hz, 1H), 8.12 (s, 1H), 7.65 (d, J=10 Hz, 1H), 3.08 (s, 1H), 1.62 (s, 9H), 1.58 (s, 9H).

2-(tert-Butoxyoxalyl-amino)-5-ethynyl-benzoic acid tert-butyl ester (0.36 g, 1.04 mmol) was treated with 50% trifluoroacetic acid/dichloromethane (15 ml) at room temperature for 3 h. The reaction mixture was concentrated in vacuo and the residue was washed with water and diethyl ether affording after drying 0.21 g (86%) of the title compound.

$^1$H NMR (400 MHz, DMSO-d$_6$) δ 8.23 (d, J=10 Hz, 1H), 8.05 (s, 1H), 7.76 (d, J=10 Hz, 1H), 4.24 (s, 1H). LC/MS [M-H]⁻: 232.07 HPLC (254.4 nm): 3.112 s, (49%).

Example 24

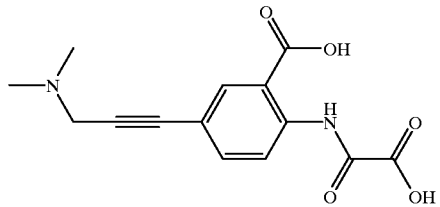

5-(3-Dimethylamino-prop-1-ynyl)-2-(oxalyl-amino)-benzoic acid;

To a solution of 5-Iodoanthranilic acid (3.0 g, 11.4 mmol) and N,N-diisopropylethylamine (4 ml, 22.8 mmol) in anhydrous tetrahydrofuran (40 ml) was added imidazol-1-yl-oxo-acetic acid tert-butyl ester (4.47 g, 22.8 mmol). The reaction was stirred at room temperature for 3 h. The solvents were evaporated in vacuo and the crude mixture extracted into ethyl acetate (70 ml). The organic extract was washed with 1% hydrochloric acid (2×15 ml) and brine (10 ml) and the solvent was evaporated in vacuo affording 2.8 g (63%) of 2-(tert-butoxyoxalyl-amino)-5-iodo-benzoic acid as a solid.

$^1$H NMR (400 MHz, CDCl$_3$) δ 8.57 (d, J=9 Hz, 1H), 8.43 (d, J=2 Hz, 1H), 8.00 (dd, J=9 Hz, 2 Hz, 1H), 1.59 (s, 9H).

To a solution of 2-(tert-butoxyoxalyl-amino)-5-iodo-benzoic add (2.1 g, 5.37 mmol) in dichloromethane (15 ml) under nitrogen was added triethylamine (3.75 ml, 26.85 mmol) and N,N-dimethylaminopyridine (0.1 g). Methoxymethyl chloride (1.2 ml, 16.11 mmol) was added and the reaction mixture was stirred for 4 h and concentrated in vacuo to a minimum volume which was loaded directly onto a silica gel column, eluting with 50% ethyl acetate/hexane. Pure fractions were combined and concentrated to give 1.5 g (64%) of 2-(tert-butoxyoxalyl-amino)-5-iodo-benzoic acid methoxymethyl ester as a solid.

$^1$H NMR (400 MHz, CDCl$_3$) δ 8.56 (d, J=9 Hz, 1H), 8.42 (s, 1H), 7.89 (d, J=9 Hz, 1H), 5.54 (s, 2H), 3.60 (s, 3H), 1.61 (s, 9H).

A solution of 2-(tert-butoxyoxalyl-amino)-5-iodo-benzoic acid methoxymethyl ester (0.16 g, 0.37 mmol), triethylamine (51 µl, 0.37 mmol) and 1-dimethylamino-2-propyne (0.12 ml, 1.11 mmol) was prepared in anhydrous acetonitrile (3 ml) and purged with argon. Dichlorobis-(triphenylphosphine)palladium (II) (5 mg, 0.0074 mmol) and copper(I) iodide (1 mg, 0.0074 mmol) were added and the reaction stirred at 60° C. under argon for 18 h. The volatiles were evaporated in vacuo and the residue redissolved in ethyl acetate (10 ml). The organic phase was washed with 1% hydrochloric acid (5 ml) and the aqueous phase extracted with additional ethyl acetate. The combined organic extracts were washed with brine (5 ml), dried (Na$_2$SO$_4$) and concentrated to an oil. The crude oil was dissolved in dichloromethane and purified by silica gel chromatography using 5% methanol/dichloromethane/0.1% triethylamine as eluent. Pure fractions were combined to give 81 mg (60%) of 2-(tert-butoxyoxalyl-amino)-5-(3-dimethylamino-prop-1-ynyl)benzoic acid methoxymethyl ester as an oil.

$^1$H NMR (400 MHz, CDCl$_3$) δ 12.52 (s, 1H), 8.75 (d, J=9 Hz, 1H), 8.21 (s, 1H), 7.64 (d, J=9 Hz, 1H), 5.53 (s, 2H), 3.59 (s, 3H), 3.46 (s, 2H), 2.38 (s, 6H), 1.61 (s, 9H).

2-(tert-Butoxyoxalyl-amino)-5-(3-dimethylamino-prop-1-ynyl)-benzoic acid methoxymethyl ester (32.3 mg) was treated with 50% trifluoroacetic acid/dichloromethane (3 ml) at room temperature for 2 h. The mixture was concentrated to a solid in vacuo and the resulting solid was washed with dichloromethane which afforded 20 mg (83%) of the idle compound as a solid.

¹H NMR (400 MHz, DMSO-d₆) δ 8.60 (d, J=9 Hz, 1H), 8.05 (s, 1H), 7.60 (d, J=9 Hz, 1H), 4.07 (s, 2H), 2.73 (s, 6H).

Example 25

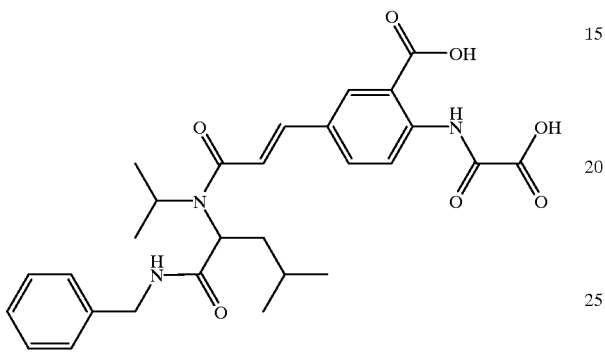

5-(2-((1-Benzylcarbamoyl-3-methyl-butyl)-isopropyl-carbamoyl)-vinyl)-2-(oxalyl-amino)-benzoic acid:

5-(2-((1-Benzylcarbamoyl-3-methyl-butyl)-isopropyl-carbamoyly)-vinyl)-2-(tert-butoxyoxalyl-amino)-benzoic acid methoxymethyl ester (0.14 g, 0.22 mmol, prepared as described in Example 33) was treated with a solution of 50% trifluoroacetic acid/dichloromethane (6 ml) for 2.5 h. The mixture was concentrated in vacuo and precipitated from water. The resulting crystalline solid was filtered off and dried in vacuo to give 0.10 g (85%) of the title compound as a solid.

¹H NMR (400 MHz, CD₃OD) δ 8.76 (d, J=9 Hz, 1H), 8.31 (s, 1H), 7.94 (d, J=9 Hz, 1H), 7.49 (d, J=16 Hz, 1H), 7.46–7.38 (m, 5H), 7.13 (d, J=16 Hz, 1H), 4.49 (m, 1H), 4.10 (s, 2H), 3.95 (m, 1H), 2.49 (m, 1H), 1.90 (m, 1H), 1.56 (m, 1H), 1.38 (d, J=6 Hz, 3H), 1.35 (d, J=7 Hz, 3H), 0.97 (d, J=6 Hz, 6H). LC/MS [M-H]⁻: 522.55.

The following compounds were prepared in a similar way as described in Example 1.

Example 26

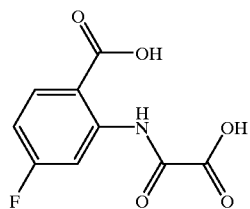

4-Fluoro-2-(oxalyl-amino)-benzoic acid;

¹H NMR (300 MHz, DMSO-d₆) δ 7.11 (m, 1H), 8.12 (m, 1H), 8.42 (dd, 1H), 12.62 (s, 1H, NHCO).

Example 27

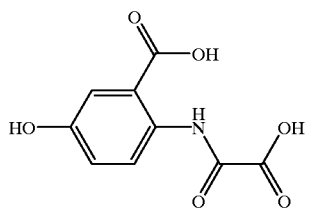

5-Hydroxy-2-(oxalyl-amino)-benzoic acid;

¹H NMR (400 MHz, DMSO-d₆) δ 12.19 (s, 1H) 9.78 (bs, 1H) 8.44 (d, J=10 Hz, 1H), 7.42 (d, J=2 Hz, 1H), 7.05 (dd, J=10 Hz, 2 Hz).

Example 28

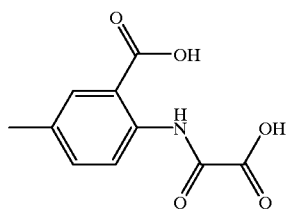

5-Methyl-2-(oxalyl-amino)-benzoic acid;

¹H NMR (400 MHz, DMSO-d₆) δ 12.20 (s, 1H), 8.51 (d, J=10 Hz, 1H), 7.83 (d, J=2 Hz, 1H), 7.42 (dd, J=10 Hz, 2 Hz, 1H), 2.29 (s, 3H).

Example 29

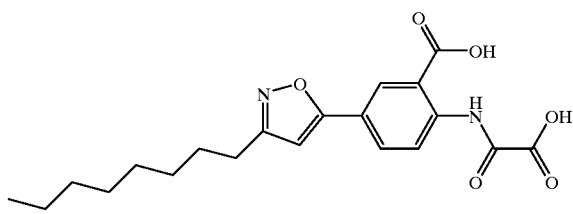

5-(3-Octyl-isoxazol-5-yl)-2-(oxaly-amino)-benzoic acid;

To a solution of 2-(tert-butoxyoxalyl-amino)-5-iodo-benzoic acid (1.8 g, 4.6 mmol) and potassium carbonate (1.6 g, 11.5 mmol) in acetone (15 ml) was added iodomethane (3 g). The reaction was heated at reflux for 2 h. after which it was judged complete by TLC analysis. The crude mixture was diluted with ethyl acetate (75 ml), washed with water (2×15 ml), and brine (10 ml). The organic phase was concentrated in vacuo to give 1.8 g (94%) of 2-(tert-butoxyoxalyl-amino)-5-iodo-benzoic acid methyl ester.

¹H NMR (400 MHz, CDCl₃) δ 12.52 (s, 1H), 8.53 (d, J=9 Hz, 1H), 8.39 (s, 1H), 8.87 (d, J=9 Hz, 1H), 3.98 (s, 3H), 1.61 (s, 9H).

2-(tert-Butoxyoxalyl-amino)-5-iodo-benzoic acid methyl ester (0.86 g, 2.12 mmol), trimethylsilyl acetylene (2 ml), and triethylamine (1.2 ml, 8.48 mmol) were dissolved in N,N-dimethylformamide (5 ml) and the solution purged with argon. Dichlorobis-(triphenylphosphine)palladium (II) (30 mg, 0.042 mmol) and copper(I)iodide (4 mg, 0.021 mmol) were added and the reaction stirred at 60° C. under argon for 3 h. The crude mixture was diluted with ethyl acetate (40 ml) and washed with water (3×10 ml) and brine (2×10 ml). The organic phase was evaporated in vacuo to yield 0.8 g (99%) of 2-(tert-Butoxyoxalyl-amino)-5-trimethylsilanylethyny-benzoic acid methyl ester which was used without further purification.

2-(tert-Butoxyoxalyl-amino-5-trimethylsilanylethyny-benzoic acid methyl ester (0.15 g, 0.4 mmol) was dissolved in tetrahydrofuran (2 ml) and treated with a 0.9 M solution of tetrabutylammonium fluoride and acetic acid (2:3) in tetrahydrofuran (0.44 ml, 0.4 mmol) for 3 h. The volatiles were evaporated in vacuo and the crude material extracted into ethyl acetate (25 ml). The ethyl acetate extract was washed with 1 N hydrochloric acid (5 ml), saturated sodium bicarbonate (5 ml), brine (5 ml) and evaporated in vacuo affording 0.1 g (83%) of 2-(tert-butoxyoxalyl-amino)-5-ethynyl-benzoic acid methyl ester as an oil.

A solution of 2-(tert-butoxyoxalyl-amino)-5-ethynyl-benzoic acid methyl ester (0.1 g, 0.33 mmol) and nonaldoxime (0.15 g, 0.99 mmol) in tetrahydrofuran (3 ml) was treated with bleach (0.75 N, 1.3 ml, 0.99 mmol). The reaction was stirred at room temperature for 24 h. TLC analysis showed presence of starting material so the reaction was heated to 35° C. for 12 h. The solvents were removed in vacuo and the crude material was dissolved in ethyl acetate (35 ml), washed with water (2×10 ml) and brine (10 ml). The organic extract was evaporated in vacuo affording 0.1 g (66%) of 2-(tert-butoxyoxalyl-amino)-5-(3-octyl-isoxazol-4-yl)-benzoic acid methyl ester as an oil.

$^1$H NMR (400 MHz, CDCl$_3$) δ 8.89 (d, J=10 Hz, 1H), 8.52 (d, J=1 Hz, 1H), 7.97 (dd, J=10, 1 Hz, 1H), 6.41 (s, 1H), 4.02 (s, 3H), 2.73 (t, J=8 Hz, 2H), 1.70 (m, 2H), 1.62 (s, 9H), 1.37–1.25 (bm, 12H), 0.89 (t, J=8 Hz, 3H).

To a solution of the above (isoxazol-4-yl)-benzoic acid methyl ester (9.1 mg, 0.02 mmol) in 50% methanovtetrahydrofuran (2 ml) was added 1 N lithium hydroxide (60 μl, 0.06 mmol) and the resulting mixture was stirred at room temperature for 48 h. The reaction was judged to be incomplete by TLC analysis (30% methanol/dichloromethane) and additional 1 N lithium hydroxide was added (20 μl, 0.02 mmol). The reaction was stirred for another 72 hours. pH of the reaction mixture was adjusted to around 0 by addition of 1 N hydrochloric acid. The mixture was concentrated in vacuo and the crude material was dissolved in ethyl acetate (20 ml). The organic layer was washed with brine (2×5 ml) and concentrated in vacuo affording 5.4 mg (70%) of the title compound as a solid.

$^1$H NMR (400 MHz, CD$_3$OD) δ 8.87 (d, J=10 Hz, 1H), 8.55 (s, 1H), 8.04 (d, J=10 Hz, 1H), 6.74 (s, 1H), 2.70 (t, J=8 Hz, 2H), 1.72 (m, 2H), 1.38 –1.20 (bm, 12H), 0.09 (t, J=8 Hz, 3H).

Example 30

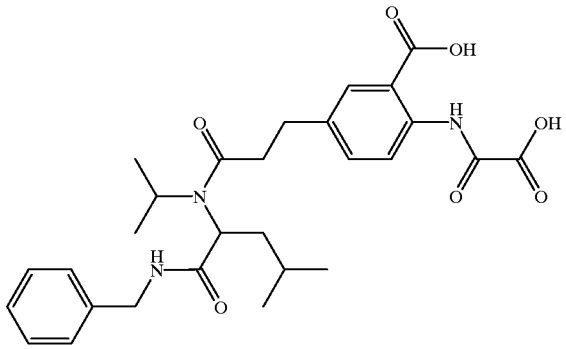

5-(2-((1-Benzylcarbamoyl-methyl-butyl)-isopropyl-carbamoyl)-ethyl)-2-(oxalyl-amino)-benzoic acid;

To a solution of isopropylamine (0.43 ml, 5.0 mmol) in methanol (5 ml) was added isovaleraldehyde (0.54 ml, 5.0 mmol). After 15 minutes of stirring a solution of benzylisocyanide in tetrahydrofuran (1N, 5 ml, 5.0 mmol) was added followed by acrylic acid (0.34 ml, 5.0 mmol). The reaction was stirred at room temperature for 72 h, the volatiles were removed in vacuo and the resulting oil dissolved in ethyl acetate (40 ml). The organic mixture was washed with 1N hydrochloric acid (10 ml) and brine (10 ml), dried (Na$_2$SO$_4$) and the solvent evaporated in vacuo. The crude residue was purified by chromatography using a gradient from 30% ethyl acetate/hexane to 50% ethyl acetate/hexane. Pure fraction were collected and the solvent evaporated in vacuo which afforded 1.5 g (100%) of N-(1-benzylcarbamoyl-3-methyl-butyl-N-isopropyl-acrylamide as an oil.

$^1$H NMR (400 MHz, CDCl$_3$) δ 8.13 (bs, 1H), 7.30–7.19 (m, 5H), 6.49 (dd, J=16 Hz, 12 Hz, 1H), 6.25 (d, J=16 Hz, 1H), 5.66 (d, J=12 Hz, 1H), 4.38 (d, J=6 Hz, 2H), 4.10–4.02 (m, 1H), 2.22–2.13 (m, 1H), 1.76–1.70 (m, 1H), 1.62–1.54 (m, 2H), 1.25 (d, J=7 Hz, 3H), 1.20 (d,J=7 Hz, 3H), 0.94 (d, J=7 Hz, 3H), 0.90 (d, J=7 Hz, 3H).

A solution of N-(1-benzylcarbamoyl-3-methyl-butyl)-N-isopropyl-acrylamide (0.55 g, 1.74 mmol), 2-(tert-butoxyoxalyl-amino)-5-iodo-benzoic acid methoxymethyl ester (0.5 g, 1.15 mmol), palladium acetate (3.0 mg, 0.023 mmol) and tri(o-tolyl)phosphine (10.0 mg, 0.07 mmol) in N,N-dimethylformamide under argon and heated to 100° C. with stirring for 3 h. The reaction was cooled to room temperature and diluted in ethyl acetate (50 ml). The organic phase was washed with water (2×15 ml) and brine (10 ml), dried (Na$_2$SO$_4$) and evaporated in vacuo. The crude oily material was purified by chromatography using 30% ethyl acetate/hexane as eluent. Pure fractions were collects and the solvent evaporated in vacuo affording 0.15 g (20%) of 5-(2-((1-Benzylcarbamoyl-3-methyl-butyl)-isopropyl-carbamoyl)-vinyl)-2-(tert-butoxyoxalyl-amino)-benzoic acid methoxymethyl ester as an oil.

$^1$H NMR (400 MHz, CDCl$_3$) δ 12.58 (s, 1H), 8.82 (d, J=9 Hz, 1H), 8.22 (s, 1H), 7.80 (d, J=9 Hz, 1H), 7.60 (d, J=16 Hz, 1H), 7.30–7.22 (m, 5H), 6.80 (d, J=16 Hz, 1H), 5.58 (s, 2H), 4.43 (bs, 2H), 4.21–4.15 (m, 1H), 3.60 (s, 3H), 2.21–2.16 (m, 1H), 1.82–1.78 (m, 1H), 1.61 (s, 9H), 1.61–1.58 (m, 1H), 1.35 (d, J=7 Hz, 3H), 1.24 (t, J=7 Hz, 3H), 0.99 (d, J=7 Hz, 3H), 0.94 (d, J=7 Hz, 3H).

To a solution of 5-(2-((1-Benzylcarbamoyl-3-methyl-butyl)-isopropyl-carbamoyl)-vinyl)-2-(tert-butoxyoxalyl-amino)-benzoic acid methoxymethyl ester (10.7 mg, 0.017 mmol) in methanol (1 ml) was added 5% palladium/carbon (2.2 mg) and the resulting mixture was stirred under hydrogen gas (30 psi) for 3 h. The mixture was filtered through celite and evaporated in vacuo. NMR indicated that the reaction was not complete so it was subjected to the hydrogenation conditions for another 4 h. The mixture was filtered and evaporated in vacuo again affording 8.9 mg (83%) of 5-(2-((1-benzylcarbamoyl-3-methyl-butyl)-isopropyl-carbamoyl)-ethyl-2-(tert-butoxyoxalyl-amino)-benzoic acid methoxymethyl ester as an oil.

$^1$H NMR (400 MHz, CDCl$_3$) δ 12.41 (s, 1H), 8.68 (d, J=9 Hz, 1H), 8.07 (bs, 1H), 7.98 (s, 1H), 7.43 (d, J=9 Hz, 1H), 7.30–7.22 (m, 5H), 5.52 (s, 2H), 4.45–4.33 (m, 2H), 4.04–3.96 (m, 2H), 3.58 (s, 3H), 2.95 (t, J=7 Hz, 2H), 2.72–2.61 (m, 2H), 2.30 (m, 1H), 1.62 (s, 9H), 1.59 (m, 1H partially obscured by neighboring singlet), 1.22 (d, J=6 Hz, 6H), 0.95 (d, J=7 Hz, 3H), 0.91 (d, J=7 Hz, 3H).

5-(2-((1-Benzylcarbamoyl-3-methyl-butyl)-isopropyl-carbamoyl)-ethyl)-2-(tert-butoxyoxalyl-amino)-benzoic acid methoxymethyl ester (4 mg, 0.0064 mmol) was dissolved in acetone (3 ml) and treated with 3 drops of 1N hydrochloric acid. The reaction was stirred for 2 days, after which the acetone was evaporated in vacuo. The residue was dissolved in ethyl acetate (10 ml), washed with brine (2×2 ml) and evaporated in vacuo. The resulting oil was treated with 20% trifluoroacetic acid/dichloromethane (3 ml) for 3 h. The volatiles were evaporated in vacuo affording 2 mg (61%) of the title compound as an oil.

$^1$H NMR (400 MHz, CD$_3$OD) δ 8.64 (d, J=9 Hz, 1H), 8.00 (s, 1H), 7.51 (d, J=9 Hz, 1H), 7.50–7.40 (m, 5H), 4.17 (t, J=8 Hz, 1H), 4.14 (s, 2H), 3.73 (m, 1H), 2.95 (t, J=6 Hz, 2H), 2.82–2.63 (m, 2H), 2.42 (m, 1H), 1.80 (m, 1H), 1.30 (m, 1H), 1.26 (d, J=6 Hz, 3H), 1.10 (d, J=6 Hz, 3H), 0.90 (d, J=6 Hz, 6H). LC/MS [M-H]$^-$: 524.74

Example 31

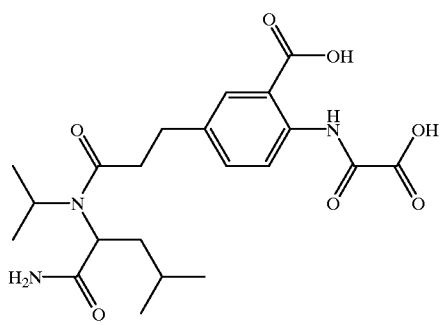

5-(2-((1-Carbamoyl-3-methyl-butyl)-isopropyl-carbamoyl)-ethyl)-2-(oxalyl-amino)-benzoic acid;

5-(2-((1-Benzylcarbamoyl-3-methyl-butyl)-isopropyl-carbamoyl)-vinyl)-2-(oxalyl-amino)-benzoic acid (33 mg, 0.063 mmol) and 10% palladium/carbon was mixed in methanol (3 ml) and stirred under hydrogen gas (1 atm) for 18 h. The mixture was filtered through celite and the volatiles were evaporated in vacuo affording 27 mg (99%) of the title compound.

$^1$H NMR (400 MHz, CD$_3$OD) δ 8.64 (d, J=9 Hz, 1H), 8.00 (s, 1H), 7.51 (d, J=9 Hz, 1H), 4.17 (t, J=8 Hz, 1H), 3.72 (m, 1H), 2.96 (t, J=6 Hz, 2H), 2.82–2.63 (m, 2H), 2.41 (m, 1H), 1.80 (m, 1H), 1.30 (m, 1H), 1.25 (d, J=6 Hz, 3H), 1.13 (d, J=6 Hz, 3H), 0.90 (d, J=6 Hz, 6H). LC/MS [M-H]$^-$: 435.66

Example 32

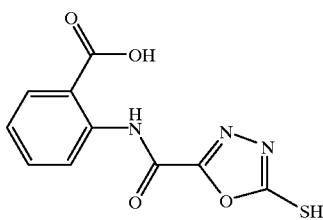

2-((5-Mercapto-[1,3,4]oxadiazole-2-carbonyl)-amino)-benzoic acid;

To a solution of 2-(Ethoxyoxalyl-amino)-benzoic acid (2.0 g, 8.43 mmol) in ethanol (75 ml) was added hydrazine hydrate (0.8 g, 16.86 mmol). The resulting mixture was stirred at reflux temperature for 3 h. To the cooled reaction was added water (200 ml) and the mixture was acidified with 1 N hydrochloric acid to pH=4. The precipitate was filtered off, washed with water and dried in vacuo at 50° C. for 16 h which afforded 1.4 g (69%) of 2-(hydrazinooxalyl-amino)-benzoic acid as a solid.

To a solution of the above 2-(hydrazinooxalyl-amino)-benzoic acid (1.0 g, 4.15 mmol) in methanol (20 ml) cooled to 0° C. was added potassium hydroxide (0.5 g, 8.72 mmol) and carbondisulfide (0.7 g, 9.54 mmol). The resulting mixture was stirred at reflux temperature for 6 h. To the cooled reaction was added water (100 ml) and the mixture was acidified with 1 N hydrochloric acid to pH=1. The precipitate was filtered off, washed with water and heptane and dried in vacuo at 50° C. The dried product (0.65 g) was purified by silica gel (400 ml) chromatography using 5% acetic acid in ethyl acetate as eluent. Pure fractions were collected and the volatiles were evaporated in vacuo. The residue was washed with water and dried in vacuo at 50° C. for 16 h affording 0.4 g (36%) of the title compound as a solid.

M.p.: 236–237° C.; Calculated for C$_{10}$H$_7$N$_3$O$_4$S; C, 45.28%; H, 2.66%; N, 15.84%. Found: C, 45.48%; H, 2.66%; N, 15.36%.

Example 33

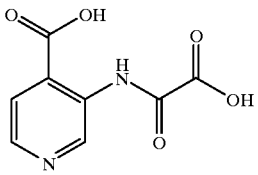

3-(Oxalyl-amino)-isonicotinic acid;

To a stirred solution of 3-amino-isonicotinic acid (0.5 g, 3.62 mmol) and triethylamine (1 ml) in dry tetrahydrofuran (50 ml) at 0° C. was added dropwise ethyl oxalyl chloride (0.5 g, 3.69 mmol). The resulting reaction mixture was stirred at room temperature for 3 h, filtered and the volatiles were evaporated in vacuo. To the residue was added water (50 ml) and the resulting mixture was extracted with diethyl ether (2×50 ml). The organic phase was washed with saturated aqueous sodium chloride (50 ml), dried (MgSO$_4$), filtered and the solvent evaporated in vacuo affording 0.4 g (46%) of 3-(ethoxyoxalyl-amino)-isonicotinic acid as a solid.

To a solution of the above isonicotinic acid (0.4 g, 1.7 mmol) in ethanol (25 ml) was added a solution of sodium hydroxide (141 mg, 3.53 mmol) in water (10 ml). The resulting reaction mixture was stirred at room temperature for 18 h. The volatiles were evaporated in vacuo and the residue dissolved in water (50 ml) and washed with diethyl ether (50 ml). To the aqueous phase was added 1N hydrochloric acid to pH=1. The precipitate was filtered off and dried in vacuo at 50° C. for 18 h. The dried solid residue was washed with boiling acetone (50 ml) for 5 min. filtered off and dried in vacuo at 50 ° C. affording 80 mg (22%) of the title compound as a solid.

M.p.: >250° C.; Calculated for C$_8$H$_6$N$_2$O$_5$; C, 45.72%; H, 2.88%; N, 13.33%. Found: C, 45.62%; H, 2.98%; N, 13.04%.

Example 34

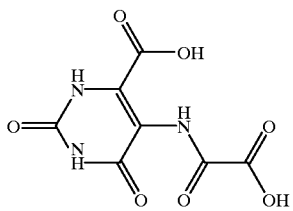

5-(Oxalyl-amino)-2,6ioxo-1,2,3,6-tetrahydro-pyrimidine-4-carboxylic acid;

To a solution of 5-aminoorotic acid (61.1 mg, 0.36 mmol) in tetrahydrofuran (1 ml) was added imidazol-1-yl-oxo-acetic acid tert-butyl ester (140 mg, 0.71 mmol) and triethylamine (50 µl, 0.36 mmol). The mixture was stirred at room temperature for 20 h. The solvent was removed in vacuo and the residue was dissolved in ethyl acetate (5.0 ml) and washed with 1% hydrochloric acid (2×2 ml) then water (2×2 ml). The organic phase was dried ($MgSO_4$), filtered and the solvent evaporated in vacuo. The residue was purified by preparative TLC (Kieselgel 60$F_{254}$, 0.5 mm, hexane:ethyl acetate, 80:20) which afforded 30 mg (28%) of 5-(tert-butoxyoxalyl-amino)-2,6-dioxo-1,2,3,6-tetrahydro-pyrimidine-4-carboxylic acid as a solid.

$^1$H NMR (400 MHz, $CDCl_3$) δ 1.80 (s, 9H), 7.56 (s, 2H), 8.96 (s, 1H).

5-(tert-Butoxyoxalyl-amino)-2,6-dioxo-1,2,3,6-tetrahydro-pyrimidine-4-carboxylic acid (28 mg, 0.094 mmol) was stirred in 20% trifluoroacetic acid in dichloromethane (1.0 ml) at room temperature for 2 h. The reaction mixture was co-evaporated in vacuo with toluene to complete dryness which afforded 22.6 mg (100%) of the title compound as a solid.

$^1$H NMR (400 MHz, $CD_3OD$) δ 7.30 (s, 2H).

Example 35

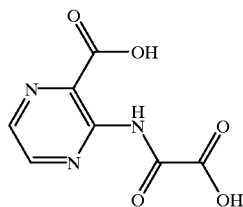

3-(Oxalyl-amino)-pyrazine-2-carboxylic acid;

To a solution of 3-aminopyrazine-2-carboxylic acid (64.2 mg, 0.46 mmol) in tetrahydrofuran (1 ml) was added imidazol-1-yl-oxo-acetic acid tert-butyl ester (181 mg, 0.92 mmol) and triethylamine (64.3 µl, 0.46 mmol). The mixture was stirred at room temperature for 20 h. The solvent was removed in vacuo and the residue was dissolved in ethyl acetate (5.0 ml) and washed with 1% hydrochloric acid (2×2 ml) then water (2×2 ml). The organic phase was dried ($MgSO_4$), filtered and the solvent evaporated in vacuo. The residue was washed with diethyl ether (4×1.0 ml) affording 48 mg (39%) of 3-(tert-butoxyoxalyl-amino)-pyrazine-2-carboxylic acid as a solid.

$^1$H NMR ($CDCl_3$+$CD_3OD$) δ 1.70 (s, 9H), 8.02 (d, 1H, J=1.5 Hz), 8.36 (d, 1H, J=1.5 Hz).

3-(tert-Butoxyoxalyl-amino)-pyrazine-2-carboxylic acid (31.7 mg, 0.12 mmol) was stirred in 20% trifluoroacetic acid in dichloromethane (1 ml) at room temperature for 2 h. The volatiles were evaporated in vacuo and the residue co-evaporated with toluene in vacuo affording 25 mg (100%) of the title compound as a solid.

$^1$H NMR (400 MHz, $CDCl_3$) δ 7.80 (d, 1H, J 1.5 Hz), 8.15 (d, 1H, J=1.5 Hz), 8.62 (s, 1H).

Example 36

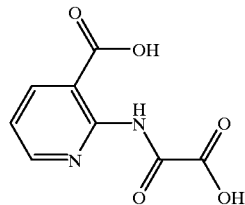

2-(Oxalyl-amino)-nicotinic acid;

To a solution of 2-aminonicotinic acid (61.4 mg, 0.45 mmol) in tetrahydrofuran (1 ml) was added imidazol-1-yl-oxo-acetic acid tert-butyl ester (174.2 mg, 0.89 mmol) and triethylamine (62 µl, 0.45 mmol). The mixture was stirred at room temperature for 2 h. The solvent was removed in vacuo and the residue was dissolved in ethyl acetate (5.0 ml) and washed with 1% hydrochloric acid (2×2 ml) then water (2×2 ml). The organic phase was dried ($MgSO_4$), filtered and the solvent evaporated in vacuo. The residue (125 mg) was purified by preparative TLC (Kieselgel 60$F_{254}$, 1 mm, $CH_2Cl_2$/MeOH, 80/20) affording 7.9 mg (7%) of 2-(tert-butoxyoxalyl-amino)-nicotinic acid as a solid.

$^1$H NMR (400 MHz, $CD_3OD$) δ 1.80 (s, 9H), 7.40 (m, 1H), 8.50–8.70 (m, 2H).

2-(tert-Butoxyoxalyl-amino)-nicotinic acid (7.1 mg, 0.03 mmol) was stirred in 20% trifluoroacetic acid in dichloromethane (0.5 ml) at room temperature for 2 h. The volatiles were evaporated to dryness in vacuo affording 5.6 mg (100%) of the title compound as a solid.

$^1$H NMR (400 MHz, $CD_3OD$) δ 7.40 (m, 1H), 8.50–8.70 (m, 2H).

Example 37

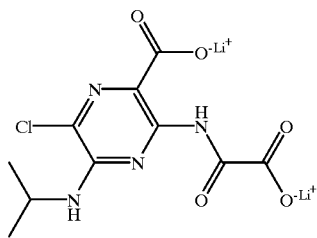

6-Chloro-5-isopropylamino-3-(oxalyl-amino)-pyrazine-2-carboxylic acid, dilithium salt;

To a solution of 3-amino-6-chloro-5-isopropylamino-pyrazine-2-carboxylic acid (65.4 mg, 0.27 mmol) in tetrahydrofuran (1 ml) was added imidazol-1-yl-oxo-acetic acid tert-butyl ester (104.8 mg, 0.54 mmol) and triethylamine (37.4 µl, 0.27 mmol). The mixture was stirred at room temperature for 20 h followed by heating to 50° C. for 1.5 h. The solvent was removed in vacuo and the residue was dissolved in ethyl acetate (5.0 ml) and washed with 1% hydrochloric acid (2×2 ml) then water (2×2 ml). The organic phase was dried ($MgSO_4$), filtered and the solvent evaporated in vacuo affording crude 97 mg (97%) of 3-(tert-butoxyoxalyl-amino)-6-chloro-5-isopropylamino-pyrazine-2-carboxylic acid as an oil.

$^1$H NMR (400 MHz, CDCl$_3$) δ 1.50 (d, 6H), 1.80 (s, 9H), 4.10 (s, 3H), 4.40 (m, 1H).

3-(tert-Butoxyoxalyl-amino)-6-cholo-5-isopropylamino-pyrazine-2-carboxylic acid (30 mg, 0.1 mmol) was dissolved in tetrahydrofuran (1 ml) and 1.0 N lithium hydroxide (1 ml, 1 mmol) was added at room temperature. The reaction mixture was stirred for 3 days at room temperature. After removing the solvent in vacuo, the residue was dissolved in ethyl acetate (20 ml) and washed with water (4×3.0 ml). The organic phase was dried (Na$_2$SO$_4$), filtered and the solvent evaporation in vacuo affording 21 mg (82%) of the title compound as a solid.

$^1$H NMR (400 MHz, CD$_3$OD) δ 1.42 (d, 6H), 4.50 (m, 1H). MS m/z 228 (M−74).

Example 38

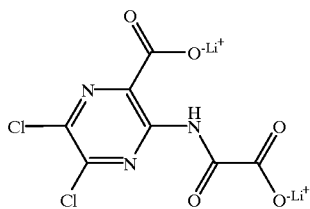

5,6-Dichloro-3-(oxalyl-amino)-pyrazine-2-carboxylic acid, dilithium salt;

To a solution of 3-amino-5,6-dichloro-pyrazine-2-carboxylic acid (57 mg, 0.26 mmol) in tetrahydrofuran (0.5 ml) was added imidazol-1-yl-oxo-acetic acid tert-butyl ester (100.6 mg, 0.513 mmol) and triethylamine (35.8 μl, 0.26 mmol). The mixture was stirred at room temperature for 20 h followed by heating at 40° C. for 4 h. The solvent was removed in vacuo and the residue was dissolved in ethyl acetate (5.0 ml) and washed with 1% hydrochloric acid (2×2 ml) then water (2×2 ml). The organic phase was dried (MgSO$_4$), filtered and the solvent evaporated in vacuo. The residual oil was purified by preparative tlc (Kieselgel 60F$_{254}$, 1 mm, hexane: ethyl acetate, 1:1) affording 23.6 mg (26%) of 3-(tert-butoxyoxalyl-amino)-5,6-dichloro-pyrazine-2-carboxylic acid as an oil.

$^1$H NMR (400 MHz, CDCl$_3$) δ 1.58 (s, 9H), 1.80 (s, 9H), 3.90 (s, 3H).

To a solution of 3-(tert-Butoxyoxalyl-amino)-5,6-dichloropyrazine-2-carboxylic acid (23 mg, 0.07 mmol) in tetrahydrofuran (0.5 ml) was added a 1.0 N aqueous solution of lithium hydroxide (0.5 ml) and the resulting mixture was stirred for 3 days. After removing the solvent in vacuo, the residue was dissolved in ethyl acetate (20 ml) and washed with water (4×3.0 ml). The organic phase was dried (Na$_2$SO$_4$), filtered and the solvent evaporation in vacuo affording 14 mg (80%) of the title compound as a solid.

MS m/z 290.3 (M−74).

What is claimed is:

1. A compound of Formula 1

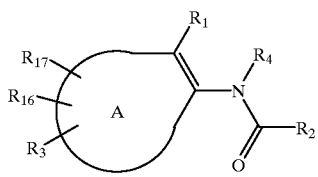

Formula 1 wherein

A is together with the double bond in Formula 1 biphenyl, indenyl, fluorenyl or fluorenyl-9-one;

R$_1$ is hydrogen, COR$_5$, OR$_6$, CF$_3$, nitro, cyano, SO$_3$H, SO$_2$NR$_7$R$_8$, PO(OH)$_2$, CH$_2$PO(OH)$_2$, CHFPO(OH)$_2$, CF$_2$PO(OH)$_2$, C(=NH)NH$_2$, NR$_7$R$_8$ or selected from the following 5-membered heterocycles:

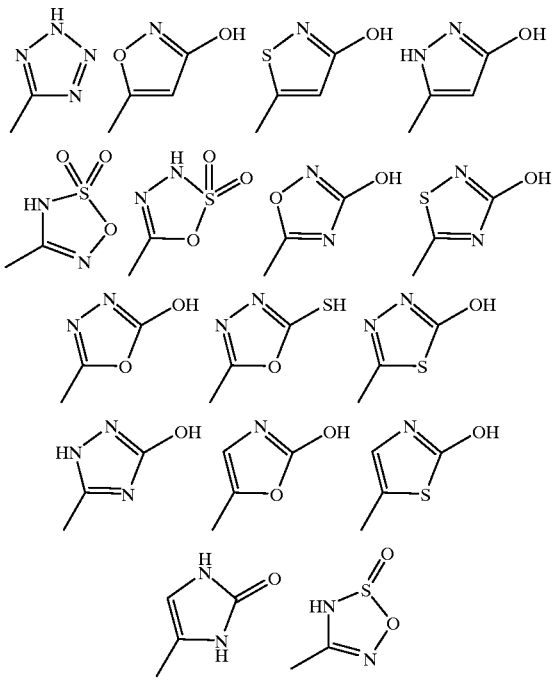

or R$_1$ is

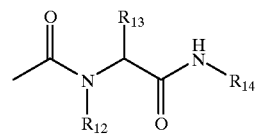

wherein R$_{12}$, R$_{13}$, and R$_{14}$ are independently hydrogen, C$_1$–C$_6$alkyl, aryl, or arylC$_1$–C$_6$alkyl wherein the alkyl and aryl groups are optionally substituted;

R$_2$ is COR$_5$, OR$_6$, CF$_3$, nitro, cyano, SO$_3$H, SO$_2$NR$_7$R$_8$, PO(OH)$_2$, CH$_2$PO(OH)$_2$, CHFPO(OH)$_2$, CF$_2$PO(OH)$_2$, C(=NH)NH$_2$, NR$_7$R$_8$, or selected from the following 5-membered heterocycles:

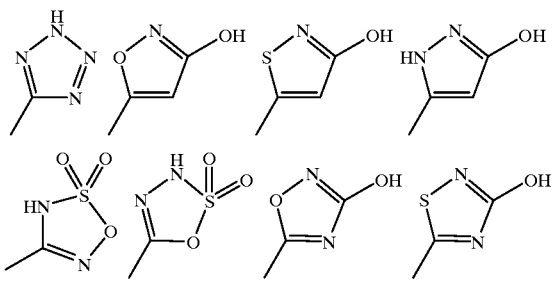

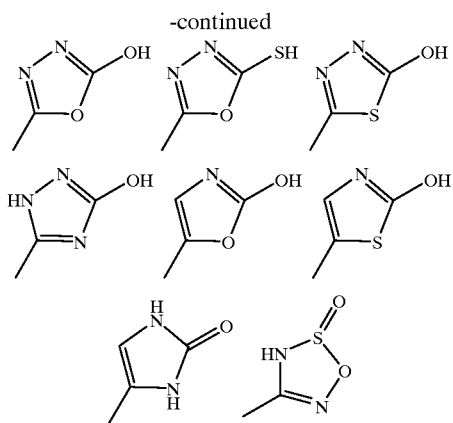

$R_3$, $R_{16}$ and $R_{17}$ are independently hydrogen, halo, nitro, cyano, trihalomethyl, $C_1$–$C_6$alkyl, aryl, aryl$C_1$–$C_6$-alkyl, hydroxy, carboxy, carboxy$C_1$–$C_6$alkyl, $C_1$–$C_6$alkyloxycarbonyl, aryloxycarbonyl, aryl$C_1$–$C_6$alkyloxycarbonyl, $C_1$–$C_6$alkyloxy, $C_1$–$C_6$alkyloxy$C_1$–$C_6$alkyl, aryloxy, aryl$C_1$–$C_6$alkyloxy, aryl$C_1$–$C_6$alkyloxy$C_1$–$C_6$alkyl, thio, $C_1$–$C_6$alkylthio, $C_1$–$C_6$alkylthio$C_1$–$C_6$alkyl, arylthio, aryl$C_1$–$C_6$alkylthio, aryl$C_1$–$C_6$alkylthio$C_1$–$C_6$alkyl, $NR_7R_8$, $C_1$–$C_6$alkylamino$C_1$–$C_6$alkyl, aryl$C_1$–$C_6$alkylamino$C_1$–$C_6$alkyl, di(aryl$C_1$–$C_6$alkyl)amino$C_1$–$C_6$alkyl, $C_1$–$C_6$alkylcarbonyl, $C_1$–$C_6$alkylcarbonyl-$C_1$–$C_6$alkyl, aryl$C_1$–$C_6$alkylcarbonyl, aryl$C_1$–$C_6$alkylcarbonyl$C_1$–$C_6$alkyl, $C_1$–$C_6$alkylcarboxy, $C_1$–$C_6$alkylcarboxy$C_1$–$C_6$-alkyl, arylcarboxy, arylcarboxy$C_1$–$C_6$alkyl, aryl$C_1$–$C_6$alkylcarboxy, aryl$C_1$–$C_6$alkylcarboxy$C_1$–$C_6$alkyl, $C_1$–$C_6$alkylcarbonylamino, $C_1$–$C_6$alkylcarbonylamino$C_1$–$C_6$alkyl, -carbonyl$NR_7C_1$–$C_6$alkyl$COR_{11}$, aryl$C_1$–$C_6$alkylcarbonylamino, aryl$C_1$–$C_6$alkylcarbonyl-amino$C_1$–$C_6$alkyl, $CONR_7R_8$, or $C_1$–$C_6$alkyl$CONR_7R_8$ wherein the alkyl and aryl groups are optionally substituted and $R_{11}$ is $NR_7R_8$, or $C_1$–$C_6$alkyl$NR_7R_8$; or $R_3$ is

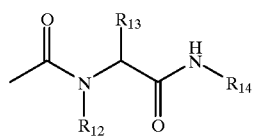

wherein $R_{12}$, $R_{13}$, and $R_{14}$ are independently hydrogen, $C_1$–$C_6$alkyl, aryl, or aryl$C_1$–$C_6$alkyl, wherein the alkyl and aryl groups are optionally substituted;

$R_4$ is hydrogen, hydroxy, $C_1$–$C_6$alkyl, aryl, aryl$C_1$–$C_6$alkyl, $NR_7R_8$, or $C_1$–$C_6$alkyloxy, wherein the alkyl and aryl groups are optionally substituted;

$R_5$ is hydroxy, $C_1$–$C_6$alkyl, aryl, aryl$C_1$–$C_6$alkyl, $C_1$–$C_6$alkyloxy, $C_1$–$C_6$alkyl-oxy$C_1$–$C_6$alkyloxy, aryloxy, aryl$C_1$–$C_6$alkyloxy, $CF_3$, or $NR_7R_8$, wherein the alkyl and aryl groups are optionally substituted;

$R_6$ is hydrogen, $C_1$–$C_6$alkyl, aryl, or aryl$C_1$–$C_6$alkyl, wherein the alkyl and aryl groups are optionally substituted;

$R_7$ and $R_8$ are independently selected from hydrogen, $C_1$–$C_6$alkyl, aryl, aryl$C_1$–$C_6$alkyl, $C_1$–$C_6$alkylcarbonyl, arylcarbonyl, aryl$C_1$–$C_6$alkylcarbonyl, $C_1$–$C_6$alkylcarboxy or aryl$C_1$–$C_6$alkylcarboxy wherein the alkyl and aryl groups are optionally substituted; or $R_7$ and $R_8$ are taken together with the nitrogen to which they are attached forming a saturated, partially saturated or aromatic cyclic, bicyclic or tricyclic ring system containing from 3 to 14 carbon atoms and from 0 to 3 additional heteroatoms selected from nitrogen, oxygen or sulfur, the ring system being optionally substituted with at least one $C_1$–$C_6$alkyl, aryl, aryl$C_1$–$C_6$alkyl, hydroxy, oxo, $C_1$–$C_6$alkyloxy, aryl$C_1$–$C_6$alkyloxy, $C_1$–$C_6$alkyloxy$C_1$–$C_6$alkyl, $NR_9R_{10}$ or $C_1$–$C_6$alkylamino$C_1$–$C_6$alkyl, wherein $R_9$ and $R_{10}$ are independently selected from hydrogen, $C_1$–$C_6$alkyl, aryl, aryl$C_1$–$C_6$alkyl, $C_1$–$C_6$alkylcarbonyl, arylcarbonyl, aryl$C_1$–$C_6$alkylcarbonyl, $C_1$–$C_6$alkylcarboxy or aryl$C_1$–$C_6$alkylcarboxy, wherein the alkyl and aryl groups are optionally substituted; or $R_7$ and $R_8$ are independently a saturated or partially saturated cyclic 5, 6 or 7 membered amine, imide or lactam;

or a salt thereof with a pharmaceutically acceptable acid or base, or any optical isomer or mixture of optical isomers, or any tautomeric forms.

2. A compound according to claim 1 wherein A is indenyl.

3. A compound according to claim 1 wherein A is fluorenyl.

4. A compound according to claim 1 wherein A is fluorenyl-9-one.

5. A compound according to claim 1 wherein A is biphenyl.

6. A pharmaceutical composition comprising an effective amount of a compound of claim 1 together with a pharmaceutically acceptable carrier or diluent.

7. The pharmaceutical composition according to claim 6 in the form of an oral dosage unit or parenteral dosage unit.

8. The pharmaceutical composition according to claim 6, wherein the compound is administered as a dose in a range from about 0.05 to 1000 mg per day.

9. 4-(Oxalyl-amino)-biphenyl-3-carboxylic acid, or a pharmaceutically acceptable salt thereof.

10. A method of inhibiting an intracellular or membrane-associated protein tyrosine phosphatase (PTPase), the method comprising exposing the PTPase to a compound of claim 1, the exposing being effected by administering said compound to a mammal in need of such inhibition.

11. The method of claim 10, wherein the mammal has a disease selected from the group consisting of autoimmune diseases, acute and chronic inflammation, osteoporosis, and various forms of cancer and malignant diseases.

12. The method of claim 10, wherein the mammal has a disease selected from the group consisting of type I diabetes, type II diabetes and obesity.

13. The method of claim 10, wherein the PTPase is PTP1B.

* * * * *